US012778466B2

(12) United States Patent
Moalem

(10) Patent No.: US 12,778,466 B2
(45) Date of Patent: Nov. 3, 2026

(54) OXYGEN SATURATION MAPPING FOR INTRAORAL SCANNING

(71) Applicant: ALIGN TECHNOLOGY, INC., San Jose, CA (US)

(72) Inventor: Yosi Moalem, Ness-Ziona (IL)

(73) Assignee: Align Technology, Inc., San Jose, CA (US)

( * ) Notice: Subject to any disclaimer, the term of this patent is extended or adjusted under 35 U.S.C. 154(b) by 241 days.

(21) Appl. No.: 18/657,319

(22) Filed: May 7, 2024

(65) Prior Publication Data

US 2024/0374180 A1 Nov. 14, 2024

Related U.S. Application Data

(60) Provisional application No. 63/500,828, filed on May 8, 2023.

(51) Int. Cl.
*A61B 5/00* (2006.01)
*A61B 5/1455* (2006.01)
(Continued)

(52) U.S. Cl.
CPC .......... *A61B 5/14552* (2013.01); *A61B 5/743* (2013.01); *A61C 9/0053* (2013.01);
(Continued)

(58) Field of Classification Search
CPC ... A61B 5/14552; A61B 5/743; A61B 5/0088; A61C 9/0053; A61C 13/34; G06T 19/20; G06T 2219/2012; G06T 2219/2024
See application file for complete search history.

(56) References Cited

U.S. PATENT DOCUMENTS

| | | | | |
|---|---|---|---|---|
| 6,099,314 A | 8/2000 | Kopelman et al. | | |
| 6,263,223 B1 * | 7/2001 | Shepherd ............. | A61B 5/6855 600/340 | |

(Continued)

FOREIGN PATENT DOCUMENTS

| | | | | |
|---|---|---|---|---|
| AU | 2021221577 A1 * | 1/2022 | ........... | A63B 71/085 |
| CN | 116829057 A * | 9/2023 | ........... | A61B 5/0088 |

(Continued)

OTHER PUBLICATIONS

Intraoral scanners for in vivo 3D (Year: 2022).*

*Primary Examiner* — May A Abouelela
(74) *Attorney, Agent, or Firm* — FisherBroyles, LLP

(57) ABSTRACT

A system of generating a blood oxygen saturation map of a patient's gingiva may include an intraoral scanner, a display, a processor, and memory comprising instructions. The instructions when executed by the processor may cause the system to generate, using the intraoral scanner, 3D scan data of a first portion of a dentition of a patient including a first portion of a gingiva of the patient. The system may generate, using the intraoral scanner, blood oxygen saturation data for the first portion of the dentition of the patient including the first portion of the gingiva of the patient and map the blood oxygen saturation data of the first portion of the gingiva of the patient to the 3D scan data. The system may display, on the display, the 3D model of the dentition of the patient with feedback indicating locations of blood oxygen saturation below a threshold.

20 Claims, 12 Drawing Sheets

(51) Int. Cl.

| | |
|---|---|
| ***A61C 9/00*** | (2006.01) |
| ***A61C 13/34*** | (2006.01) |
| ***G06T 19/20*** | (2011.01) |

(52) U.S. Cl.

CPC .............. *A61C 13/34* (2013.01); *G06T 19/20* (2013.01); *G06T 2219/2012* (2013.01); *G06T 2219/2024* (2013.01)

(56) References Cited

U.S. PATENT DOCUMENTS

| | | | |
|---|---|---|---|
| 6,334,772 | B1 | 1/2002 | Taub et al. |
| 6,334,853 | B1 | 1/2002 | Kopelman et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |
| 6,664,986 | B1 | 12/2003 | Kopelman et al. |
| 6,697,164 | B1 | 2/2004 | Babayoff et al. |
| 6,845,175 | B2 | 1/2005 | Kopelman et al. |
| 6,979,196 | B2 | 12/2005 | Nikolskiy et al. |
| 7,030,383 | B2 | 4/2006 | Babayoff et al. |
| 7,202,466 | B2 | 4/2007 | Babayoff et al. |
| 7,255,558 | B2 | 8/2007 | Babayoff et al. |
| 7,286,954 | B2 | 10/2007 | Kopelman et al. |
| 7,319,529 | B2 | 1/2008 | Babayoff |
| 7,373,286 | B2 | 5/2008 | Nikolskiy et al. |
| 7,507,088 | B2 | 3/2009 | Taub et al. |
| 7,545,372 | B2 | 6/2009 | Kopelman et al. |
| 7,698,068 | B2 | 4/2010 | Babayoff |
| 7,916,911 | B2 | 3/2011 | Kaza et al. |
| 8,108,189 | B2 | 1/2012 | Chelnokov et al. |
| 8,244,028 | B2 | 8/2012 | Kuo et al. |
| 8,587,582 | B2 | 11/2013 | Matov et al. |
| 8,948,482 | B2 | 2/2015 | Levin |
| D742,518 | S | 11/2015 | Barak et al. |
| 9,192,305 | B2 | 11/2015 | Levin |
| 9,261,356 | B2 | 2/2016 | Lampert et al. |
| 9,261,358 | B2 | 2/2016 | Atiya et al. |
| 9,299,192 | B2 | 3/2016 | Kopelman |
| D760,901 | S | 7/2016 | Barak et al. |
| 9,393,087 | B2 | 7/2016 | Moalem |
| 9,408,679 | B2 | 8/2016 | Kopelman |
| 9,431,887 | B2 | 8/2016 | Boltanski |
| 9,439,568 | B2 | 9/2016 | Atiya et al. |
| 9,451,873 | B1 | 9/2016 | Kopelman et al. |
| D768,861 | S | 10/2016 | Barak et al. |
| D771,817 | S | 11/2016 | Barak et al. |
| 9,491,863 | B2 | 11/2016 | Boltanski |
| D774,193 | S | 12/2016 | Makmel et al. |
| 9,510,757 | B2 | 12/2016 | Kopelman et al. |
| 9,660,418 | B2 | 5/2017 | Atiya et al. |
| 9,668,829 | B2 | 6/2017 | Kopelman |
| 9,675,430 | B2 | 6/2017 | Verker et al. |
| 9,693,839 | B2 | 7/2017 | Atiya et al. |
| 9,717,402 | B2 | 8/2017 | Lampert et al. |
| 9,724,177 | B2 | 8/2017 | Levin |
| 9,844,426 | B2 | 12/2017 | Atiya et al. |
| 10,076,389 | B2 | 9/2018 | Wu et al. |
| 10,098,714 | B2 | 10/2018 | Kuo |
| 10,108,269 | B2 | 10/2018 | Sabina et al. |
| 10,111,581 | B2 | 10/2018 | Makmel |
| 10,111,714 | B2 | 10/2018 | Kopelman et al. |
| 10,123,706 | B2 | 11/2018 | Elbaz et al. |
| 10,136,972 | B2 | 11/2018 | Sabina et al. |
| 10,380,212 | B2 | 8/2019 | Elbaz et al. |
| 10,390,913 | B2 | 8/2019 | Sabina et al. |
| 10,453,269 | B2 | 10/2019 | Furst |
| 10,456,043 | B2 | 10/2019 | Atiya et al. |
| 10,499,793 | B2 | 12/2019 | Ozerov et al. |
| 10,504,386 | B2 | 12/2019 | Levin et al. |
| 10,507,087 | B2 | 12/2019 | Elbaz et al. |
| 10,517,482 | B2 | 12/2019 | Sato et al. |
| 10,695,150 | B2 | 6/2020 | Kopelman et al. |
| 10,708,574 | B2 | 7/2020 | Furst et al. |
| 10,772,506 | B2 | 9/2020 | Atiya et al. |
| 10,813,727 | B2 | 10/2020 | Sabina et al. |
| 10,888,399 | B2 | 1/2021 | Kopelman et al. |
| 10,952,816 | B2 | 3/2021 | Kopelman |
| 10,980,613 | B2 | 4/2021 | Shanjani et al. |
| 11,013,581 | B2 | 5/2021 | Sabina et al. |
| 11,033,750 | B1 * | 6/2021 | Radmand ................ C01B 33/20 |
| D925,739 | S | 7/2021 | Shalev et al. |
| 11,096,765 | B2 | 8/2021 | Atiya et al. |
| 11,238,586 | B2 | 2/2022 | Minchenkov et al. |
| 11,367,192 | B2 | 6/2022 | Kopelman et al. |
| 11,455,727 | B2 | 9/2022 | Minchenkov et al. |
| 11,478,132 | B2 | 10/2022 | Kopelman et al. |
| 11,563,929 | B2 | 1/2023 | Saphier et al. |
| 11,633,268 | B2 | 4/2023 | Moalem et al. |
| 11,707,238 | B2 | 7/2023 | Moshe et al. |
| RE49,605 | E | 8/2023 | Kopelman |
| 11,744,681 | B2 | 9/2023 | Kopelman et al. |
| 11,759,277 | B2 | 9/2023 | Shalev et al. |
| 11,896,461 | B2 | 2/2024 | Saphier et al. |
| 11,937,996 | B2 | 3/2024 | Peleg |
| 11,995,839 | B2 | 5/2024 | Weiss et al. |
| 2005/0288571 | A1 * | 12/2005 | Perkins ................ A61B 5/0002 600/407 |
| 2006/0001740 | A1 * | 1/2006 | Fujie .................. A61B 1/00048 348/66 |
| 2012/0295216 | A1 * | 11/2012 | Dykes .................... A61C 19/04 433/27 |
| 2013/0323673 | A1 * | 12/2013 | Hakomori .......... A61B 1/00009 433/29 |
| 2017/0290699 | A1 * | 10/2017 | Radmand ............. A61B 5/4557 |
| 2019/0209091 | A1 * | 7/2019 | Saigh ................... A61B 5/6846 |
| 2020/0038231 | A1 * | 2/2020 | Radmand ............. A61B 5/0816 |
| 2020/0170574 | A1 * | 6/2020 | Radmand ............... A61B 5/291 |
| 2021/0121049 | A1 | 4/2021 | Rudnitsky et al. |
| 2021/0137653 | A1 | 5/2021 | Saphier et al. |
| 2021/0196152 | A1 | 7/2021 | Saphier et al. |
| 2021/0236050 | A1 * | 8/2021 | Hu ....................... A61B 5/4812 |
| 2022/0110724 | A1 * | 4/2022 | Moalem ............... A61C 9/0053 |
| 2022/0189611 | A1 * | 6/2022 | Farkash ............... A61C 9/0053 |
| 2022/0240786 | A1 * | 8/2022 | Subhash .............. A61B 5/0088 |
| 2023/0021695 | A1 * | 1/2023 | Atiya ................... A61C 9/0053 |
| 2024/0029901 | A1 * | 1/2024 | Ezhov ..................... G16H 10/60 |
| 2025/0339308 | A1 * | 11/2025 | Hao ................... A61B 5/02055 |

FOREIGN PATENT DOCUMENTS

| | | | | |
|---|---|---|---|---|
| EP | 4512308 | A1 * | 2/2025 | ............. G06T 19/20 |
| ES | 2967677 | T3 * | 5/2024 | ........... A61B 5/0071 |
| KR | 20210147729 | A * | 12/2021 | ............. A61B 6/032 |
| KR | 102645173 | B1 * | 3/2024 | ............. A61C 9/004 |
| WO | WO-2019115303 | A1 * | 6/2019 | ......... A61B 5/14542 |
| WO | WO-2022051566 | A1 * | 3/2022 | ............. A61F 5/566 |
| WO | WO-2022159276 | A1 * | 7/2022 | ........... A61B 1/0646 |

* cited by examiner

OXYGEN SATURATION MAPPING FOR INTRAORAL SCANNING

RELATED APPLICATIONS

This application claims the benefit under 35 U.S.C. § 119 (e) of U.S. Provisional Patent Application No. 63/500,828, filed May 8, 2023, which is incorporated, in its entirety, by this reference.

BACKGROUND

The present disclosure is generally related to scanning and generating models of a patient's dentition and determining the health of a patient's dentition.

Blood flow and delivery of oxygen to a patient's dental tissues plays a role in the health of a patient's dentition including the teeth, gums, bones and other aspects of the patient's dentition. Poor blood flow and poor delivery of oxygen to the patient's dental tissue may suggest unhealthy gums and other dental tissues.

Dental treatments may involve orthodontic procedures for repositioning misaligned teeth and changing bite configurations for improved cosmetic appearance and/or dental function. Dental treatments may also include restorative treatment wherein bridges, implants, and other prosthetics are designed and used in order to restore the patient's dentition. Orthodontic and restorative treatments may include scanning the patient's dentition using an intraoral scanner to generate a three-dimensional model of the patient's dentition. The 3D model may be used to plan the orthodontic or restorative treatment.

Current scanning systems and methods are less than ideal for a number of reasons. For example, current scanning systems are unable to detect blood flow within the patient's gingiva and blood oxygen saturation of blood within the patient's gingiva.

In light of the above, improved devices and methods that overcome at least some of the above limitations of the prior devices and methods would be helpful.

SUMMARY

Embodiments of the present disclosure provide improved intraoral scanning systems and methods that provide accurate models of the blood oxygen saturation levels in the patient's gingiva and oral tissues.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The methods, apparatus, and systems disclosed herein are well suited for combination with prior devices such as intraoral scanners, for example the iTero system commercially available from Align Technology, Inc.

The presently disclosed methods and systems are well suited for combination with prior approaches to scanning intraoral structures, such as with generating three-dimensional models of a patient's dentition.

Figure 1:
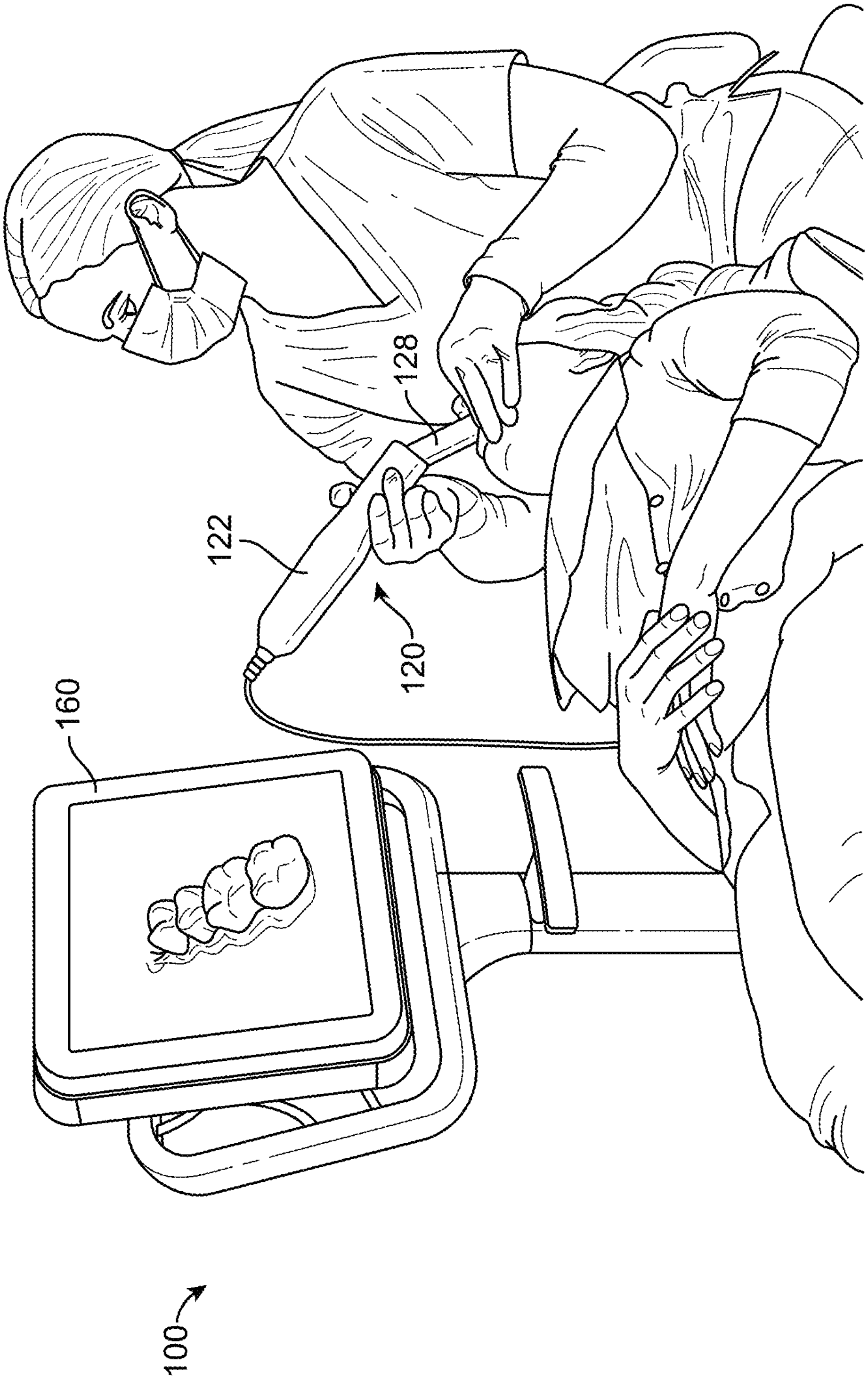
FIG. 1 shows an intraoral scanning system, in accordance with some embodiments.

Reference is now made to FIGS. 1 and 2, which are a schematic illustrations of an intraoral scanning system 100, in accordance with some embodiments of the present invention. The intraoral scanning system 100 comprises an elongate handheld wand 122 that has a probe 128 at distal end of the handheld wand 122. Probe 128 has a distal end 127 and a proximal end 124. As used herein, the proximal end of the handheld wand is the end of the handheld wand that is closest to a user's hand when the user is holding the handheld wand in a ready-for-use position and the distal end of the handheld wand is defined as the end of the handheld wand that is farthest from the user's hand when the user is holding the handheld wand in a ready-for-use position.

In some embodiments, a structured light projector 130 is disposed in proximal end 124 of probe 128, one or more imaging cameras 132 are disposed in proximal end 124 of probe 128, and a mirror 134 is disposed in distal end 127 of probe 128. Structured light projector 130 and imaging camera 132 are positioned to face mirror 134, and mirror 134 is positioned to reflect light from structured light projector 130 directly onto an object 136 being scanned and reflect light from object 136 being scanned into imaging camera 132.

Structured light projector 130 includes a light source 140. In some embodiments, structured light projector 130 may have a field of illumination of at least 6 degrees. In some embodiments, the field of illumination may be between about 6 degrees and about 30 degrees. In some embodiments, the field of illumination may be less than about 30 degrees. In some applications, structured light projector 130 focuses light from light source 140 at a projector focal plane that may be located external to the probe and at an object to be scanned 136. In some embodiments, the focal plane may be at least 30 mm from the light source 140. In some embodiments, the focal plane may be between 30 mm and 140 mm from the light source 140. In some embodiments, the light source may be less than 140 mm from light source 140. Structured light projector 130 may have a pattern generator 142 that is disposed in the optical path between light source 140 and the projector focal plane. Pattern generator 142 generates a structured light pattern at projector focal plane 138 when light source 140 is activated to transmit light through pattern generator 142.

Imaging cameras 132 may have a field of view of at least 6 degrees. In some embodiments, the field of view may be between about 6 degrees and about 30 degrees. In some embodiments, the field of view may be less than about 30 degrees. Imaging camera or cameras 132 may focus at a camera focal plane that may be located at least 30 mm from the imaging camera 132. In some embodiments, the focal plane may be between 30 mm and 140 mm from the imaging camera 132. Imaging camera 132 has an imaging camera sensor 146 that comprises an image sensor comprising an array of pixels, e.g., a CMOS image sensor. Imaging camera 132 additionally may have an objective lens 154 disposed in front of imaging camera sensor 148 that forms an image of object 136 being scanned onto imaging camera sensor 146.

Intraoral scanner 100 may include control circuitry 156 that drives structured light projector 130 to project a structured light pattern onto object 136 outside handheld wand 122 and drives imaging camera 132 to capture an image that results from the structured light pattern reflecting off object 136. The structured imaging contains information about the intensity of the structured light pattern reflecting off object 136 and the direction of the light rays. The imaging also contains information about phase-encoded depth via which the scene depth can be estimated from different directions. Using information from the captured imaging, a computer processor may reconstruct a three-dimensional image of the surface of object 136 and may output the image to an output device, e.g., a monitor. It is noted that computer processor herein, by way of illustration and not limitation, to be outside of handheld wand 122. In some embodiments, computer processor may be disposed within handheld wand 122.

In some embodiments, object 136 being scanned is at least one tooth and adjacent gingiva inside a subject's mouth. Imaging camera 132 in intraoral scanner 120 may capture the imaging from the structured light pattern reflecting off the tooth and gingiva without the presence of an opaque or other powder on the tooth, enabling a simpler digital intraoral scanning experience.

The structured light scanning system may generate point clouds representing the three-dimensional surface of the object 136 being scanned. The structured light service may generate up to 60 frames per second of point cloud data that may be used to generate a three-dimensional model of the surface of the object 136 being scanned. In some embodiments, the point cloud data may be used to determine the position and orientation of the scanning wand with respect to the intraoral structure of the object 136 being scanned.

In some embodiments, the structured light scanning system may also capture the color of the surfaces of the object 136. For example, in some embodiments the structured light source may be a white light source and the imaging camera 132 may record the color of the surface of the object 136 based on the light reflected from the object.

With reference to FIGS. 1-3, the intraoral scanning system 100 may include a blood oxygen saturation scanning and measurement system. The blood oxygen saturation scanning and measurement system may include one or more light sources for emitting red and infrared light and one or more photodetectors for detecting reflected red and infrared light reflected from an object such as object 136.

Figure 2A:
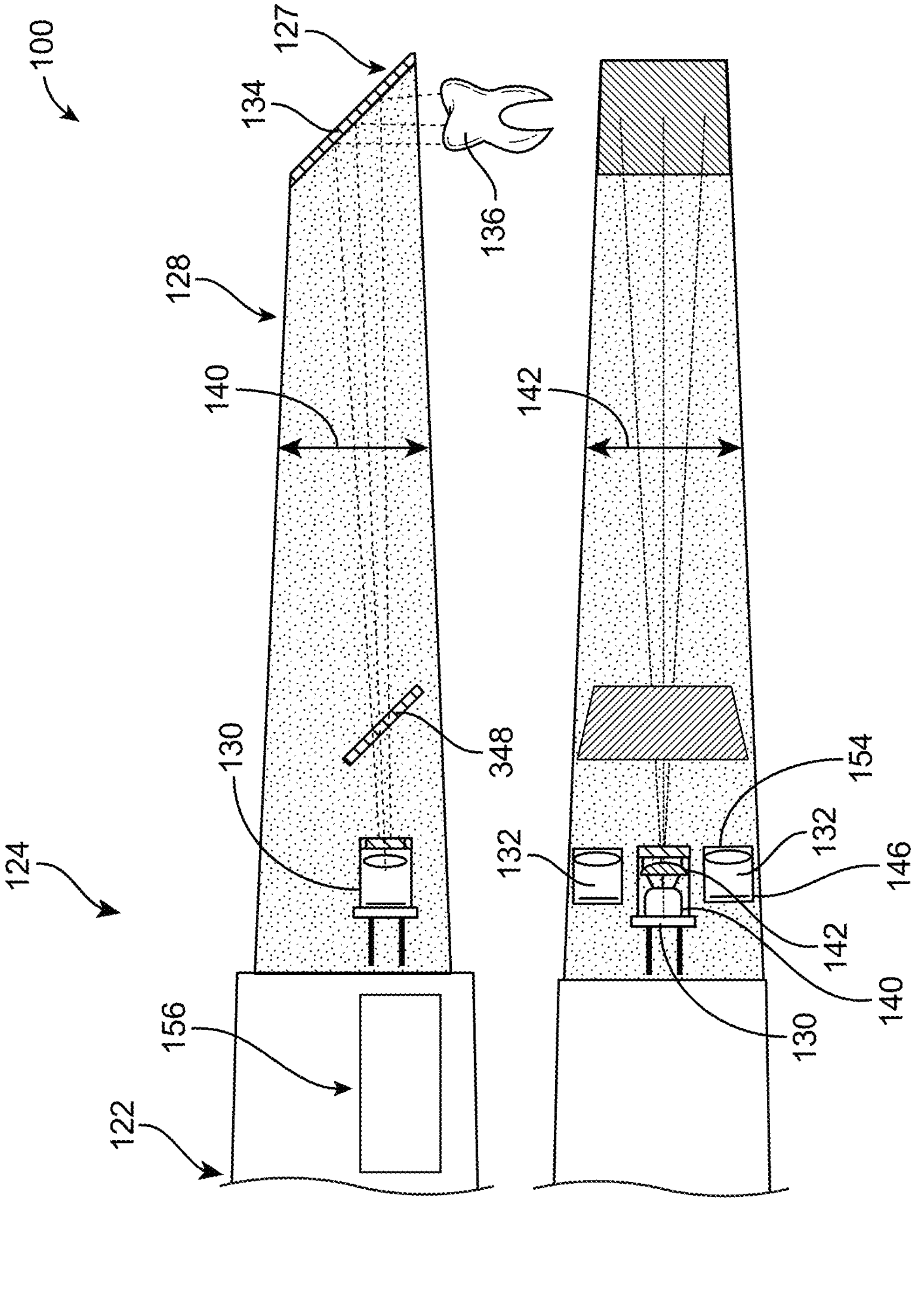
FIGS. 2A and 2B show aspects of an intraoral scanner for scanning and determining blood oxygen levels using an intraoral scanner, in accordance with some embodiments.

In some embodiments, such as shown in FIG. 2A, the light source may be the structured light emitter 130. In some embodiments, the structured light emitter 130 may include red and/or infrared light sources that pass through the distal end of the probe and illuminate the object 136.

Figure 2B:
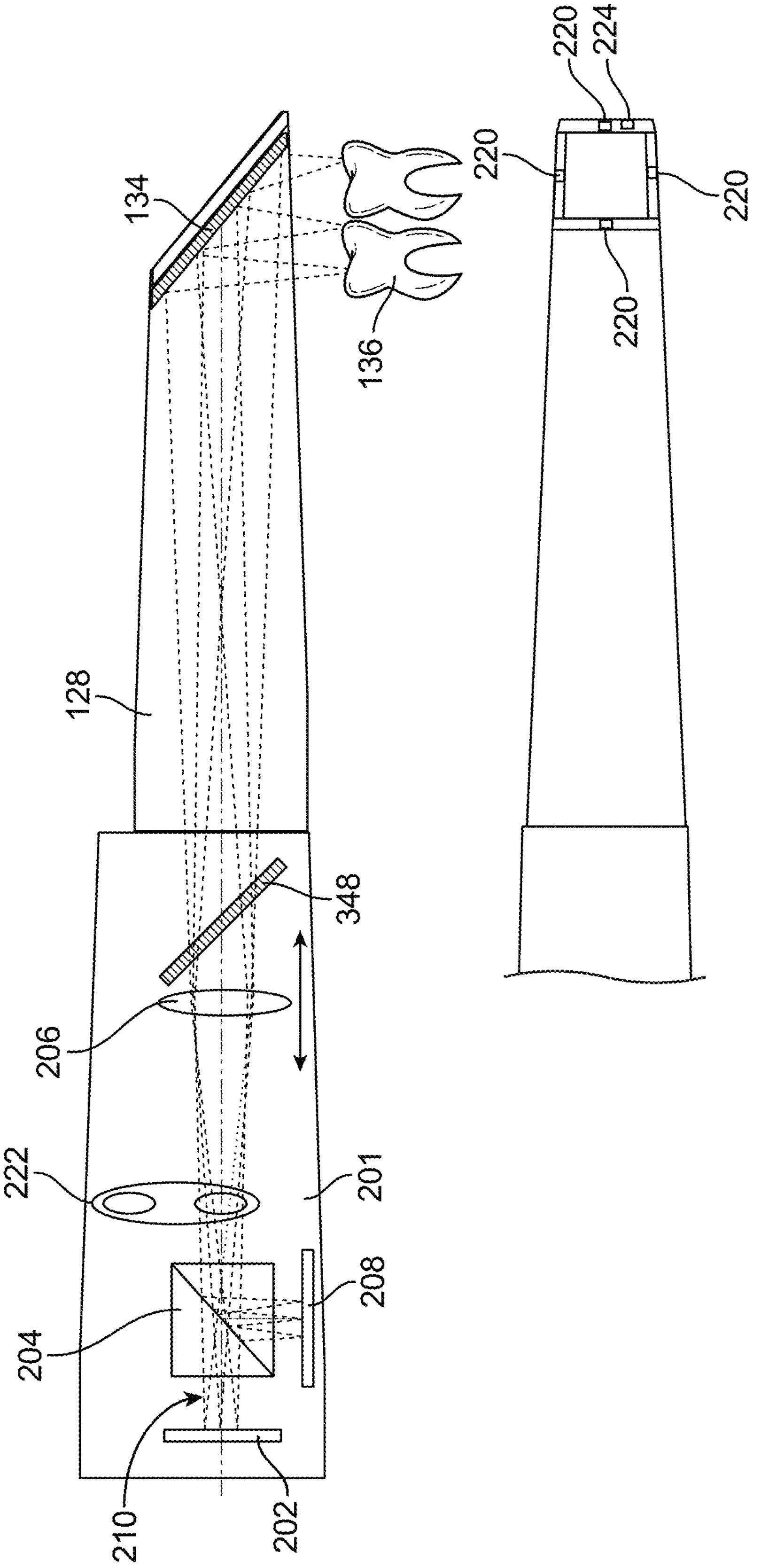

In some embodiments, such as shown in FIG. 2B, a light source may be a light sources 220 that is located at a distal end of the probe such as at or surrounding the scanning window of the intraoral scanning probe.

In some embodiments, the photodetector may be an imaging device such as imaging device 132 depicted in FIG. 2A. In the embodiment shown in FIG. 2A light emitted from within the probe is directed out of the probe to the object to be measured 136. Reflected light from the object to be measured passes back through the probe to the imaging device 132.

In some embodiments, the photodetector may be an imaging device such as imaging device 208 depicted in FIG. 2B. In the embodiment shown in FIG. 2B light emitted from light sources 220 on an external surface or at an external surface of the probe is reflected off the object to be measured 136 and travels through the probe to the photodetector 208.

While non-contact forms of blood oxygen measurement systems are discussed herein, in some embodiments, the probe may include a contact blood oxygen saturation sensor. For example, the distal end of the probe may include a light sensor 224 that is located on an external surface or at an external surface of the probe that can measure the intensity of light reflected off the object to be measured 136 without the light having passed through the probe. The light source 220 in combination with the sensos 224 may act as a contact based blood oxygen measurement system. To measure the blood oxygen saturation of a portion of a patient's detention, such as the gingiva the distal end of the probe, and in particular, the light source 220 and adjacent light sensor 224 are placed in contact with the gingiva. Red and IR light is then emitted, (in some embodiments, IR and red light is alternatively emitted) from the light source while the adjacent light sensor 224 measured the reflected light from the gingiva. The blood oxygen saturation can then be measured, as discussed herein.

In some embodiments, blood oxygen saturation scanning and measurement system may include a filter, such as filter wheel 222. The filter wheel 222 may rotate during operation of the intraoral scanner. As discussed herein, the intraoral scanner may include multiple scanning mode such as a 3D scanning mode, a color capture mode, a blood oxygen saturation capture mode, and other modes. The filter wheel may rotate and place colored filters in the light path in order to limit the wavelengths of light that pass from the emitter to the object to be measured and/or light reflected from the object to be measured to the image sensors. For example, the filter wheel may rotate to place a first filter, such as a neutral density filter, a luminance filter, or other filter that allows visible wavelengths of light to pass, in the light path when capturing color images. In some embodiments, the filter wheel may include no filter in at least one position. When imaging with structured light, the filter wheel may place a filter that allows the structured light to pass through. When imaging for detection of blood oxygen saturation, the filter wheel may place a red and/or IR filter in the light path. In some embodiments, the filter or filters may be incorporated into the image sensor wherein a first portion of pixels have an IR filter, a second portion of the pixels have a red filter for imaging during blood oxygen scanning and may be a narrow bandpass, a third portion of the pixels have a green filter, a fourth portion of pixels have a blue filter, a fourth portion of the pixels may have a second red filter for imaging during color imaging that may be a wide bandpass greater than the filter of the second portion, and a fifth portion of pixels may have a filter that allows the structure light wavelengths to pass.

The control circuitry 156 may also drive the scanning system and coordinate the illumination, filtering, and recording of the various light sources for each of the scanning modes.

For 3D scanning with structured light suing the system of 2A, when structured light projector 130 and imaging camera 132, and the object arm 340 are disposed in proximal end 124 of probe 128, the size of probe 128 is limited by the angle at which mirror 134 is placed. In some embodiments, a height 140 of probe 128 is less than 17 mm, and a width 143 of probe 128 is less than 22 mm, height 140 and width 143 defining a plane that is perpendicular to a longitudinal axis of handheld wand 122. The height 140 of probe 128 is measured from a lower surface (scanning surface), through which reflected light from object 136 being scanned enters probe 128, to an upper surface opposite the lower surface. In some embodiments, the height 140 is between 14-17 mm. In some embodiments, the width 143 is between 18-22 mm.

For 3D scanning with confocal scanning using the system of FIG. 2B the confocal system includes a patterned light source 202, a beam splitter 204, and focusing and imaging optics 206, and a color image sensor 208 located within the scanner body 201. During use, the patterned light source 202 generates a 2D light pattern such as an 2D array of light beams 210. The light beams pass through a beam splitter 204 and then through focusing and imaging optics 206. The focusing and imaging optics 206 may include one or more lenses to confocally focus the light beams on the object 136. The light beams then pass through a dichroic mirror 348 and are reflected off of the mirror 134 before illuminating the object 136. Light from the 2D array of light beams is reflected off of the object 134 back into the scanner 200. The reflect light reflects off of the mirror 134, passes through the dichroic mirror 348 and the focusing optics 206 before being reflected by the beam splitter into a color image sensor. The image sensor records an images of the light data for each part of the object. The images are then processed to generate depth data, such as point clouds, for the surface of the object 136. Many frames of depth data are then stitched together to generate a 3D model of the object.

Figure 3A:
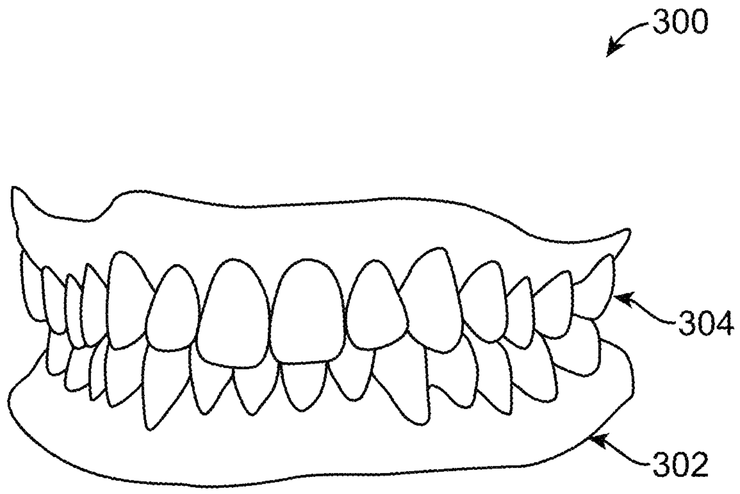
FIG. 3A shows a 3D model of the patient's dentition generated using the intraoral scanning system of FIGS. 1 and 2, in accordance with some embodiments.

FIG. 3A depicts a 3D model 300 of a patient's detention generated using any of the 3D scanning techniques discussed herein. The 3D model includes the 3D surface structure of the teeth 304 and gums 302 of the patient. The 3D model 300 may also include color data mapped to the 3D surface model based on color scanning of the patient's dentition.

Figure 3B:
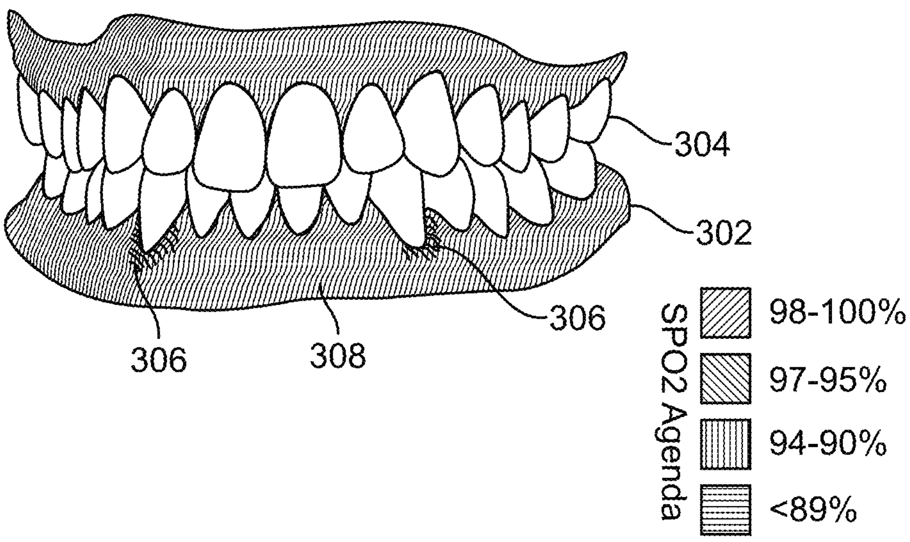
FIG. 3B shows a blood oxygen and blood flow map of the patient's dentition applied to the 3D model of FIG. 3A, in accordance with some embodiments.

FIG. 3B depicts a 3D model 350 of a patient's detention generated using any of the 3D scanning techniques discussed herein with added oxygen saturation information generated using any of the methods discussed herein. While the 3D model depicts the teeth and dentition, the 3D model may include other soft tissues of the patient's intraoral cavity and corresponding added oxygen saturation information generated using any of the methods discussed herein. The other soft tissues may include the palate, tongue, lips, checks, and other soft tissues. The 3D model includes the 3D surface structure of the teeth 304 and gums 302 of the patient. The 3D model 300 may also include color data mapped to the 3D surface model based on color scanning of the patient's dentition. The 3D surface model 350 may also include data that indicates the detected blood oxygen level of the patient's gingiva. For example, the gingiva may be highlighted, textured, or otherwise modified to include feedback or indication of the detected blood oxygen level of the patient's gingiva. For example, the gingiva 302 of 3D surface model 350 includes first and second portions 306 with hatching indicating blood oxygen levels between 95% and 97% and third portions 308 with hatching that indicates blood oxygen levels of greater than 98%. In some embodiments, the portions 306, 308 may be colored differently, such as no modified color when blood oxygen levels are above a threshold and modified colors for one or more ranges of oxygen saturation below the threshold. The ranges may be between below 90%, between 90% and 95%, between 95% and 97%, and greater than 97%.

In some embodiments, the feedback may indicate low blood oxygen levels, such as levels at which orthodontic treatment should be postponed until further evaluation can be performed or until corrected. In some embodiments, the hatching or other feedback may include highlighted areas, areas of unnatural color, such as colors not normally found on a patient's gingiva, such as yellow, orange, or black. In some embodiments, the feedback may flash or be displayed intermittently to call attention to the locations. In some embodiments, the threshold may be set by a user. For example, the system may output a request for a threshold. In some embodiments, the system may receive a threshold. In some embodiments, multiple thresholds may be requested, received, and/or used.

Blood oxygen saturation, or SpO2 measurements work on the principle that hemoglobin protein in human blood absorbs light in different amounts depending on the wavelength and whether the hemoglobin is carrying oxygen. Hemoglobin is the protein in red blood cells that carries oxygen. When the hemoglobin in the blood is fully saturated with oxygen, it absorbs more infrared light and less red light. Conversely, when the hemoglobin is less saturated with oxygen, it absorbs more red light and less infrared light. The oxygen saturation of blood may be determined based on the ration of red and infrared light absorbed by the blood. The result may be displayed as a percentage, representing the amount of hemoglobin in the blood that is saturated with oxygen.

Two wavelengths of light may be used to determine blood oxygen saturation: red light and infrared light. The red light may be in a range of approximately 650 nm to about 730 nm, preferably between 640 nm and 700 nm, and the infrared light may be between about 850 nm and about 950 nm. In some embodiments, the red light may be 700 nm and the infra-red light may be 900 nm.

Figure 4:
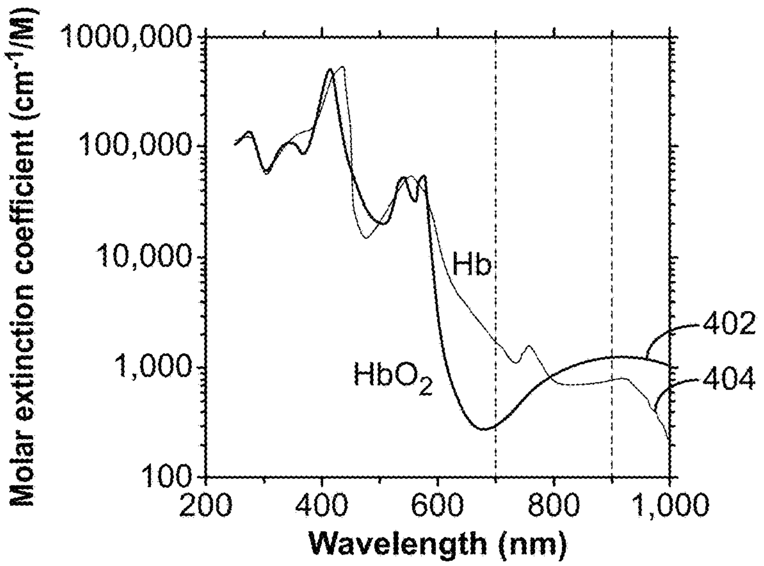
FIG. 4 shows a chart of the absorption spectra of hemoglobin, in accordance with some embodiments.
Figure 5:
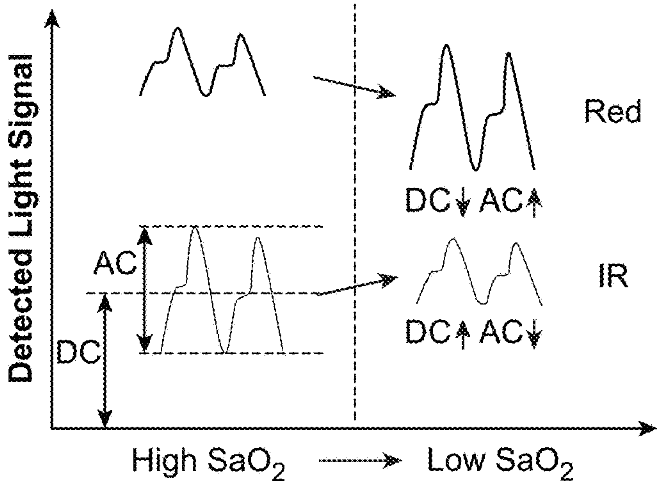
FIG. 5 shows a chart of the detected light signals of high and low $SaO_2$, in accordance with some embodiments.

With reference to FIG. 4, focusing on the red to infra-red wavelengths, the absorption of light at these wavelengths differs significantly between blood loaded with oxygen, depicted as line 402, and blood lacking oxygen, depicted as line 404.

Looking specifically at two wavelengths: 700 nm and 900 nm, the oxygenated hemoglobin absorbs more infrared light at 900 nm and allows more red light at 700 nm to pass through, while deoxygenated hemoglobin allows more infra-red light at 900 nm to pass through and absorbs more red light at 700 nm. These light absorption characteristics of hemoglobin allow for non-invasive oximeter oxygen saturation measurements.

In calculating blood oxygen saturation based on light absorption characteristics of hemoglobin, there are two factors that are used to calculate SpO2, the AC or alternating component and the and DC or constant or offset component.

The AC component represents the pulsatile changes in blood oxygen saturation as a result of blood volume and movement changes that occur with each heartbeat. As the heart beats, blood is pumped into the arteries, causing a temporary increase in blood volume and oxygenated hemoglobin in the pulsatile component of the blood. The AC component is measured by the pulse oximeter as the difference between the maximum and minimum light absorbance during a single cardiac cycle.

The DC component represents the non-pulsatile blood volume, including both the oxygenated and deoxygenated hemoglobin in the arteries and veins. The DC component is measured by the pulse oximeter as the average light absorbance over time.

The ratio of the AC component to the DC component is used to calculate SpO2. This is because the AC component primarily reflects the oxygen saturation level of arterial blood, while the DC component reflects the total amount of blood in the tissue being measured. By comparing the ratio of the AC and DC components at the two different wavelengths of light (red and infrared), the pulse oximeter can estimate the oxygen saturation level of the arterial blood.

The ratio is called the modulation ratio and may be calculated using the AC and DC components of the red and infrared signals according to the equation:

$$R = \frac{ACred/DCred}{ACir/DCir}$$

Figure 6:
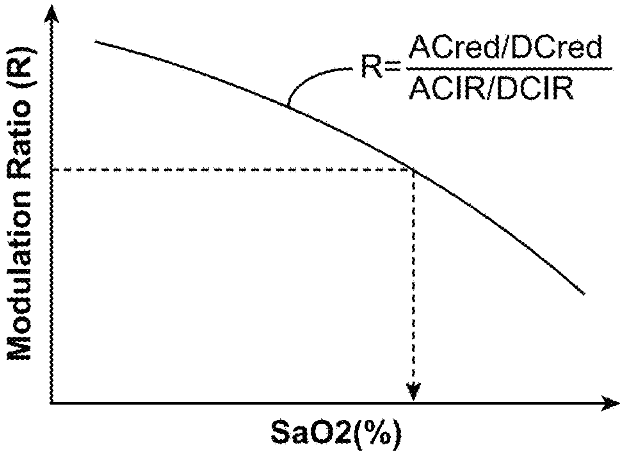
FIG. 6 shows a chart of calibrated calibration curves derived from the detected light signals of light reflected from blood for use in determining patient blood oxygen in accordance with some embodiments.

ACRED and ACIR are the AC amplitudes of the red and infrared signals, and DCRED and DCIR are the DC offsets of the red and infrared signals. FIG. 6 shows a graph that converts modulation ratio to Spo2 based on empirical calibration of a reflective oxygen saturation sensor system.

The empirical calibration of a reflective oxygen saturation sensor system may include measuring the output (such as the amount or red and infrared light reflected) of the reflective oxygen saturation sensor system at different oxygen saturation levels and comparing the output to a reference measurement. The output may also be a computer modulation ratio. The reference measurement may be obtained using a laboratory blood gas analyzer.

During the calibration process, a set of measurements is taken at various oxygen saturation levels while the person being measured is still and not moving. The light source and detector of a reflective oxygen saturation sensor system is placed on or pointed at a finger, toe, earlobe, or gingiva. The person's oxygen saturation may be adjusted to different levels by changing the amount of oxygen in the air they breathe or by adjusting other variables that affect oxygen saturation.

The reference values obtained from the laboratory blood gas analyzer are then compared to the readings, such as the modulation ratio calculated from the data gathered by the light sensor or the reflective oxygen saturation sensor system. Any differences between the two are used to adjust the calibration of the reflective oxygen saturation sensor system, such as by using regression analysis to fit a curve to the data.

The calibration function is then stored in the reflective oxygen saturation sensor system memory and used to convert the instrument's sensor data into an estimate of oxygen saturation.

Figure 7:
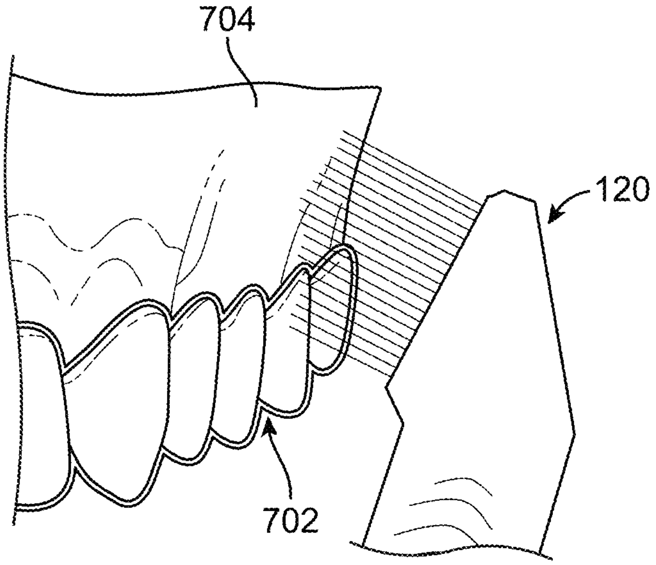
FIG. 7 shows scanning of a portion of a patient's dentition using an intraoral scanner, in accordance with some embodiments.
Figure 8:
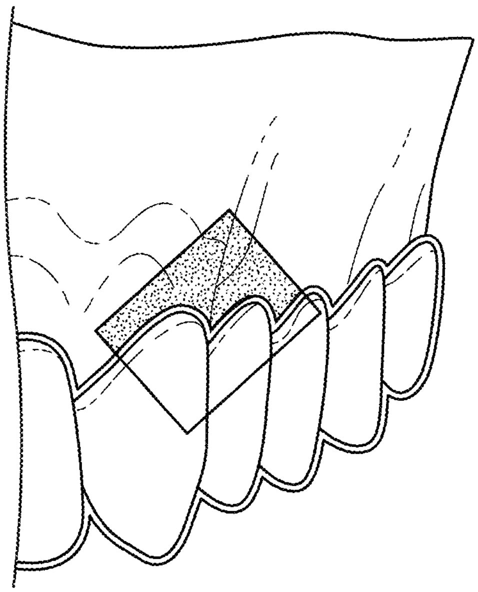
FIG. 8 shows a view of reflected light for measuring blood oxygen captured using an intraoral scanner, in accordance with some embodiments.
Figure 9:
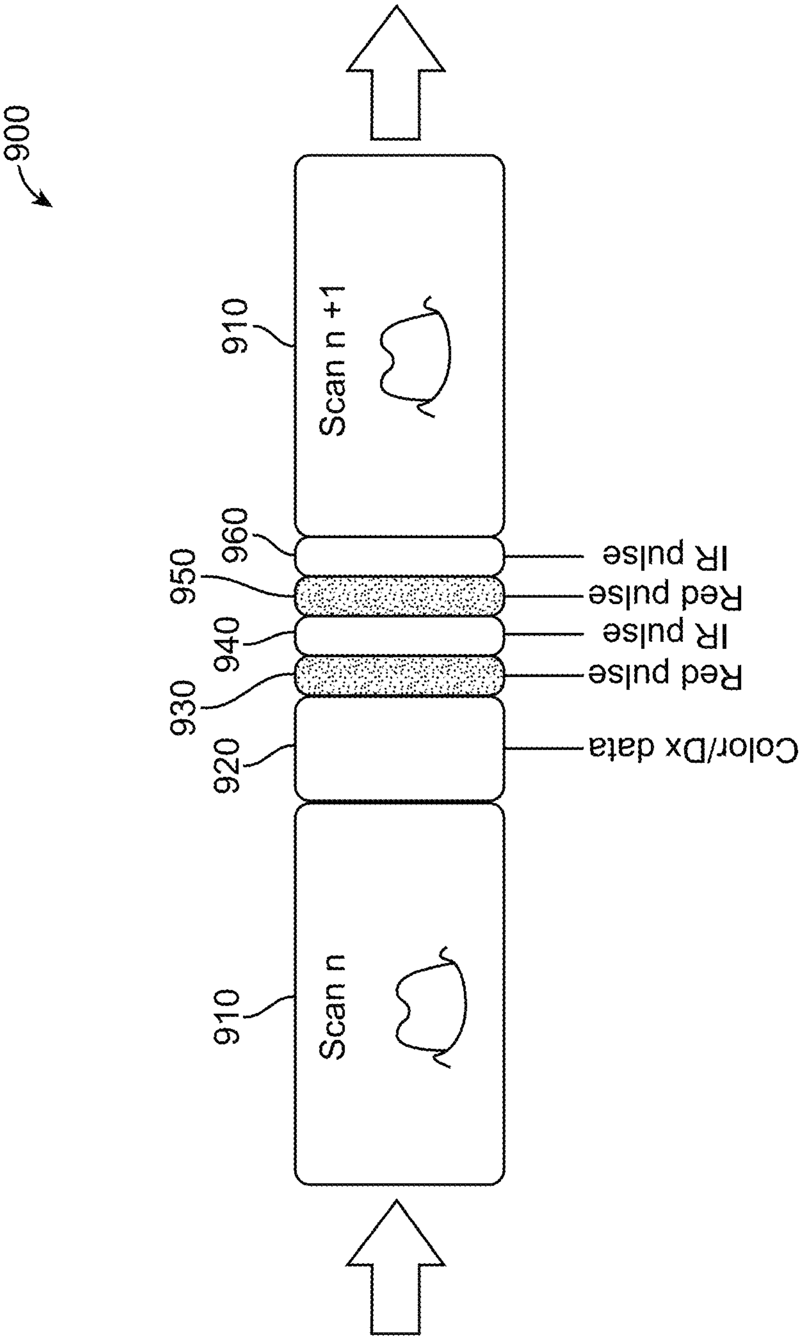
FIG. 9 shows phases of scanning and determining blood oxygen levels using an intraoral scanner, in accordance with some embodiments.

Aspects of generating a 3D model of a patient's dentition and determining blood oxygen saturation levels using an intraoral scanner are shown in FIGS. 7, 8, and 9. FIG. 7 depicts aspects of 3D scanning the patient's dentition in which structured light scan or confocal scan surface data or other 3D data is captured or generated to create a three-dimensional model of the surface structure of the patient's intraoral tissues, such as teeth and gingiva.

As shown in FIG. 7, an intraoral scanner 120, which may include aspects of the probe 100 and/or probe 200 scans a patient's dentition, which may include the teeth 702 and gingiva 704. The 3D scanning process may include capturing point cloud data. During the scanning process, the scanner emits light, such as laser or structured light that bounces off the surface of the patient's dental tissues. The image sensor in the scanner measures aspects of the returning light, such as the focus, the time of flight, phase shift, or the image of the structured light to determine the distance between the scanner and the surface. This process is repeated at different locations and angles as the intraoral scanner is moved. The scanner captures multiple point clouds overlapping point clouds, such that each location on the patient's dentition is captured at least twice and may be captured in tens or hundreds of frames or point clouds.

In some embodiments, the point clouds may be cleaned and/or filtered before being combined into a 3D model. After the point clouds are captured, they may contain noise, outliers, and other artifacts that can affect the accuracy of the 3D resulting 3D model. To clean and filter the point clouds, various algorithms are used, such as statistical outlier removal, smoothing, and hole filling. Statistical outlier removal involves identifying and removing points that are significantly different from the surrounding points based on their distance or intensity values. Smoothing involves averaging the values of neighboring points to reduce noise and create a smoother surface. Hole filling involves interpolating values for missing data or regions where the scanner was unable to capture data.

The point clouds are then combined to create a 3D model of the patient's dentition through a process called registration. Registration involves aligning the point clouds so that they are in the correct position relative to each other. There are several techniques that can be used for registration, including iterative closest point (ICP), feature-based matching, and global registration. ICP involves iteratively minimizing the distance between corresponding points in the point clouds. Feature-based matching involves identifying distinctive features of the object or environment, such as edges or corners, and using these features to find correspondences between the point clouds. Global registration may include aligning the point clouds to a common coordinate system based on known reference points or markers.

When two point clouds are registered, they may be meshed to form a surface model. The mesh may be updated when each additional point cloud is registered to the model.

In some embodiments, color data, such as 2D color images are captured as part of the scanning process. The color data can be mapped to the 3D model to generate a color 3D model of the patient's detention.

In some embodiments, the intraoral scanner scans segments of 3D data and acquires an additional data for color, teeth transparency etc. during or in between 3D scanning of segments of the patient's dentition. The system to operate hardware systems and/or illumination sources different from the ones used for 3D scanning. By capturing the color data, tooth transparency data, or other data during or as part of the 3D scanning process, the system can correlate and match the additional data to the 3D scan segment.

The intraoral scanner may also capture data of reflected red and IR light while the dentition is illuminated with red and IR light emitted from the intraoral scanner. FIG. 8 depicts a view of a captured image of red or IR light reflected off the gingiva during illumination of red or IR light from the intraoral scanner.

For implementing reflective pulse oximetry within an intraoral scanner, a red illumination source of about 700 nm and IR illumination source of about 900 nm may be used. The scanner system generates consecutive 3D scan segments, such as the point clouds discussed above. Between two consecutive 3D scan segments the system may emit and receive the reflections of two consecutive pulses of light, one a red pulse of light and the second an infrared pulse of light.

The field of view of an image sensor may capture light reflected from the teeth and the gingiva. However, SpO2 levels are not measured from the teeth because they do not have circulating blood near their surface. Instead, soft tissues such as the gingiva may be imaged in order to measure SpO2 levels. The system may analyze the last 3D scan segment or scan data and, based on the data, segment the soft tissue or gingiva from the teeth and other distance tissue. The system then, may calculate the surface area of the mouth tissue that absorbs the red and IR energy, such as the gingiva, using the 3D info of the last 3D scan segment, the next 3D scan, or an average of both the previous and next 3D scan. To normalize the R ratio to soft mouth tissue only, such as gingiva.

In some embodiments, each pixel of the red and IR light images may be mapped to a location on the patient's detention, based on the previous and next 3D scan. Then, each location may be scanned multiple times over at least 1 second, at least 2 second, at least 3 seconds, at least 4 seconds, or at least 5 seconds. As the intraoral scanners moves within the intraoral cavity to scan the patient's detention, the locations and amounts of red and IR light reflected may be tracked for each location, even as the scanner moves and the locations move within the field of view of the imaging device. From the multiple scans, such as 10 scans, 100 scans, or 1000 scans over the at least 1 second, at least 2 second, at least 3 seconds, at least 4 seconds, or at least 5 seconds the AC and DC components may be generated and the SpO2 may be determined for each location.

In some embodiments, the intraoral scanner may contact the gingiva of the patient during scanning and held in place to determine the SpO2 using a contact method and system, such as described with respect to FIG. 2B. For example, a first portion of the dentition may be scanned, then the intraoral scanner may contact the gingiva at a location on the first portion of the dentition to measure the SpO2. The location of the SpO2 measurement may be recorded, such as on a first portion of the 3D model built based on the scans of the first portion of the dentition. Then, a second portion of the dentition may be scanned, then the intraoral scanner may contact the gingiva at a second location on the second portion of the dentition to measure the SpO2. The location of the second SpO2 measurement may be recorded, such as on a second portion of the 3D model built based on the scans of the second portion of the dentition. The process may be repeated until the entire dentition is scanned.

In some embodiments, the scanner may capture SpO2 data while the patient closes their mouth or lips around the scanner. In some embodiments, the scanner may pause scanning, output, such as to a display or audio feedback, a prompt or instructions indicated the patient should close their mount and/or lips around the scanner, receive feedback indicating that the mount is closed, and then record SpO2 data. In some embodiments, the intraoral scanner may determine that the mouth and/or lips are closed, or the oral cavity is sufficiently dark to gather SpO2 data via a sensor, such as a light sensor, which may include an imaging device, such as imaging device 208 and/or a camera sensor, such as camera sensor 146.

FIG. 9 depicts a process flow 900 for measuring SpO2 of a patient's gingiva while conducing a 3D scan of the patient's dentition using an intraoral scanner. The process flow 900 may include generating first 3D scan data, such as a point cloud at block 910, capturing color data of the patient's dentition at block 920, emitting a first red pulse of light and recording the reflected red light at first red light data at block 930, emitting a first IR pulse of light and recording reflected IR light as IR light data at block 940, emitting a second red pulse of light and recording second reflected red light data at block 950, emitting a second IR pulse of light and recording second reflected IR light data at block 960, and then repeating the process until the patient's dentition is scanned.

At block 910 an intraoral scanner 120, which may include aspects of the probe 100 and/or probe 200 scans a patient's dentition, which may include the patient's teeth and gingiva. The 3D scanning process may include capturing point cloud data. During the scanning process, the scanner emits light, such as laser or structured light that bounces off the surface of the patient's dental tissues. The image sensor in the scanner measures aspects of the returning light, such as the focus, the time of flight, phase shift, or the image of the structured light to determine the distance between the scanner and the surface. This process is repeated at different locations and angles as the intraoral scanner is moved. The point cloud data may be stored for registration with additional point cloud data captured later.

In some embodiments, if a partial 3D model of previously scanned and registered point clouds exists, the captured point cloud data may be registered with the existing point cloud data or 3D model.

In some embodiments, the point clouds may be cleaned and/or filtered. After the point clouds are captured, they may contain noise, outliers, and other artifacts that can affect the accuracy of the 3D resulting 3D model. To clean and filter the point clouds, various algorithms are used, such as statistical outlier removal, smoothing, and hole filling. Statistical outlier removal involves identifying and removing points that are significantly different from the surrounding points based on their distance or intensity values. Smoothing involves averaging the values of neighboring points to reduce noise and create a smoother surface. Hole filling involves interpolating values for missing data or regions where the scanner was unable to capture data.

The point clouds may then be combined to create a 3D model of the patient's dentition through a process called registration. Registration involves aligning the point clouds so that they are in the correct position relative to each other. There are several techniques that can be used for registration, including iterative closest point (ICP), feature-based matching, and global registration. ICP involves iteratively minimizing the distance between corresponding points in the point clouds. Feature-based matching involves identifying distinctive features of the object or environment, such as edges or corners, and using these features to find correspondences between the point clouds. Global registration may include aligning the point clouds to a common coordinate system based on known reference points or markers.

When two point clouds are registered, they may be meshed to form a surface model. The mesh may be updated when each additional point cloud is registered to the model.

At block 920 color data, such as 2D color images, are captured as part of the scanning process. If the color data is captured early in the scanning process, such as before a 3D model has been generated, the color data may be stored for later mapping to a 3D model. The color data may be associated with a frame or multiple frames of captured 3D data, such as one or more point clouds. After sufficient point cloud data is captured to start building a 3D model of the patient's detention, the color data may be mapped to the 3D model based on the point cloud frame or frames to which it is associated. In some embodiments, associating may include an order in which the data is captured, such that the color data is mapped based on the 3D scan frame or point captured before or after the capture of the color data, such as immediately before or after the capture of the color data. In some embodiments, each capture is time stamped and the color data is mapped to the 3D data based on the time in which the color and 3D data is captured, such as mapping the color data based on the 3D data captured within a period of time before and/or after the capture of the color data, such as within 10 ms, 20 ms, 30 ms, 50 ms, 75 ms, 100 ms, 200 ms, or 250 ms. The color data can be mapped to the 3D model to generate a color 3D model of the patient's detention.

At block 930 an intraoral scanner may also capture data of reflected red light while the dentition is illuminated with red light emitted from the intraoral scanner. FIG. 8 depicts a view of a captured image of red reflected off the gingiva during illumination of red from the intraoral scanner.

For implementing reflective pulse oximetry within an intraoral scanner, a red illumination source of about 700 nm may be used. The scanner system generates consecutive 3D scan segments, such as the point clouds discussed above. Between two consecutive or nonconsecutive 3D scan segments the system may emit and receive the reflections of red light.

At block 930 consecutive transmit or emitting of red light pulses and corresponding or simultaneous capture of the red light reflections may be performed. The time slot associated with block 930 may include 1, 2, 3, 4, or more pulses of red light and capture of red light reflection data. Each pulse may include emitting red light with a known power calibrated to several distances from the intraoral scanner exit window. Each red light pulse illuminates for a known time period to control the energy amount of every wavelength. Each received frame of red from this time slot is analyzed to isolate the area of interest for oxygen saturation calculations. Each area of interest may be divided to M×N matrix for localization of the tissue oxygen saturation. The same M×N matrix may serve all frames of the same slot.

At block 940 consecutive transmit or emitting of IR light pulses and corresponding or simultaneous capture of the IR light reflections may be performed. The time slot associated with block 940 may include 1, 2, 3, 4, or more pulses of IR light and capture of IR light reflection data. Each pulse may include emitting IR light with a known power calibrated to several distances from the intraoral scanner exit window. Each IR light pulse illuminates for a known time period to control the energy amount of every wavelength. Each received frame of IR from this time slot is analyzed to isolate the area of interest for oxygen saturation calculations. Each area of interest may be divided to M×N matrix for localization of the tissue oxygen saturation. The same M×N matrix may serve all frames of the same slot.

At block 950 consecutive transmit or emitting of red light pulses and corresponding or simultaneous capture of the red light reflections may be performed. The time slot associated with block 950 may include 1, 2, 3, 4, or more pulses of red light and capture of red light reflection data. Each pulse may include emitting red light with a known power calibrated to several distances from the intraoral scanner exit window. Each red light pulse illuminates for a known time period to control the energy amount of every wavelength. Each received frame of red from this time slot is analyzed to isolate the area of interest for oxygen saturation calculations. Each area of interest may be divided to M×N matrix for localization of the tissue oxygen saturation. The same M×N matrix may serve all frames of the same slot.

At block 960 consecutive transmit or emitting of IR light pulses and corresponding or simultaneous capture of the IR light reflections may be performed. The time slot associated with block 940 may include 1, 2, 3, 4, or more pulses of IR light and capture of IR light reflection data. Each pulse may include emitting IR light with a known power calibrated to several distances from the intraoral scanner exit window. Each IR light pulse illuminates for a known time period to control the energy amount of every wavelength. Each received frame of IR from this time slot is analyzed to isolate the area of interest for oxygen saturation calculations. Each area of interest may be divided to M×N matrix for localization of the tissue oxygen saturation. The same M×N matrix may serve all frames of the same slot.

If the red and IR SpO2 data is captured early in the scanning process, such as before a 3D model has been generated, the red and IR SpO2 data may be stored for later mapping to a 3D model. The red and IR SpO2 data may be associated with a frame or multiple frames of captured 3D data, such as one or more point clouds. After sufficient point cloud data is captured to start building a 3D model of the patient's detention, the red and IR SpO2 data may be mapped to the 3D model based on the point cloud frame or frames to which it is associated. In some embodiments, associating may include an order in which the data is captured, such that the red and IR SpO2 data is mapped based on the 3D scan frame or point captured before or after the capture of the red and IR SpO2 data, such as immediately before or after the capture of the red and IR SpO2 data. In some embodiments, each capture is time stamped and the red and IR SpO2 data is mapped to the 3D data based on the time in which the red and IR SpO2 and 3D data is captured, such as mapping the red and IR SpO2 data based on the 3D data captured within a period of time before and/or after the capture of the red and IR SpO2 data, such as within 10 ms, 20 ms, 30 ms, 50 ms, 75 ms, 100 ms, 200 ms, or 250 ms. The red and IR SpO2 data can be mapped to the 3D model to generate a red and IR SpO2 3D model of the patient's detention.

After capturing scan data, color data, and red and IR SpO2 data, the scanning process may repeat, starting again with capture of scan data at second block 910. The process may repeat until the patient's dentition is scanned.

Figure 10:
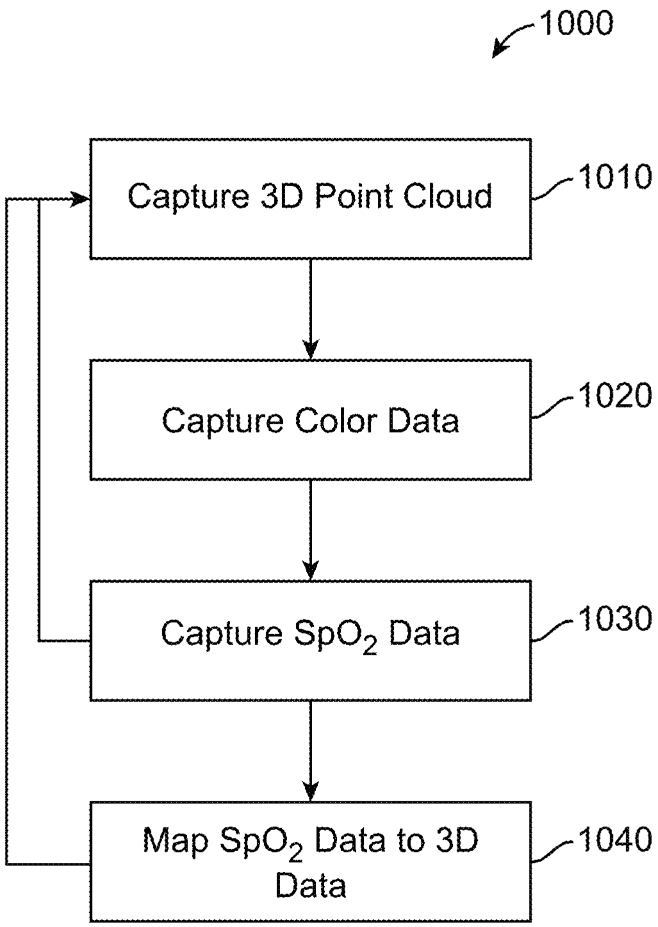
FIG. 10 shows a method of scanning and determining blood oxygen levels using an intraoral scanner, in accordance with some embodiments.

FIG. 10 depicts a process 1000 of generating a color 3D model of a patient's detention with mapped SpO2 data. The process may start at block 1010. At block 1010, an intraoral scanner 120, which may include aspects of the probe 100 and/or probe 200 scans a patient's dentition, which may include the patient's teeth and gingiva. The 3D scanning process may include capturing point cloud data. During the scanning process, the scanner emits light, such as laser or structured light that bounces off the surface of the patient's dental tissues. The image sensor in the scanner measures aspects of the returning light, such as the focus, the time of flight, phase shift, or the image of the structured light to determine the distance between the scanner and the surface. This process is repeated at different locations and angles as the intraoral scanner is moved. The point cloud data may be stored for registration with additional point cloud data captured later.

In some embodiments, if a partial 3D model of previously scanned and registered point clouds exists, the captured point cloud data may be registered with the existing point cloud data or 3D model.

In some embodiments, the point clouds may be cleaned and/or filtered. After the point clouds are captured, they may contain noise, outliers, and other artifacts that can affect the accuracy of the 3D resulting 3D model. To clean and filter the point clouds, various algorithms are used, such as statistical outlier removal, smoothing, and hole filling. Statistical outlier removal involves identifying and removing points that are significantly different from the surrounding points based on their distance or intensity values. Smoothing involves averaging the values of neighboring points to reduce noise and create a smoother surface. Hole filling involves interpolating values for missing data or regions where the scanner was unable to capture data.

The point clouds may then be combined to create a 3D model of the patient's dentition through a process called registration. Registration involves aligning the point clouds so that they are in the correct position relative to each other. There are several techniques that can be used for registration, including iterative closest point (ICP), feature-based matching, and global registration. ICP involves iteratively minimizing the distance between corresponding points in the point clouds. Feature-based matching involves identifying distinctive features of the object or environment, such as edges or corners, and using these features to find correspondences between the point clouds. Global registration may include aligning the point clouds to a common coordinate system based on known reference points or markers.

When two point clouds are registered, they may be meshed to form a surface model. The mesh may be updated when each additional point cloud is registered to the model.

At block 1020, color data may be captured. Color data, such as 2D color images, are captured as part of the scanning process. If the color data is captured early in the scanning process, such as before a 3D model has been generated, the color data may be stored for later mapping to a 3D model. The color data may be associated with a frame or multiple frames of captured 3D data, such as one or more point clouds. After sufficient point cloud data is captured to start building a 3D model of the patient's detention, the color data may be mapped to the 3D model based on the point cloud frame or frames to which it is associated. In some embodiments, associating may include an order in which the data is captured, such that the color data is mapped based on the 3D scan frame or point captured before or after the capture of the color data, such as immediately before or after the capture of the color data. In some embodiments, each capture is time stamped and the color data is mapped to the 3D data based on the time in which the color and 3D data is captured, such as mapping the color data based on the 3D data captured within a period of time before and/or after the capture of the color data, such as within 10 ms, 20 ms, 30 ms, 50 ms, 75 ms, 100 ms, 200 ms, or 250 ms. The color data can be mapped to the 3D model to generate a color 3D model of the patient's detention.

At block 1030, SpO2 data may be captured. Consecutive transmit or emitting of red light pulses and corresponding or simultaneous capture of the red light reflections may be performed. 1, 2, 3, 4, or more pulses of red light and capture of red light reflection data may be performed. Each pulse may include emitting red light with a known power calibrated to several distances from the intraoral scanner exit window. Each red light pulse illuminates for a known time period to control the energy amount of every wavelength. Each received frame of red from this time slot is analyzed to isolate the area of interest for oxygen saturation calculations. Each area of interest may be divided to M×N matrix for localization of the tissue oxygen saturation. Each pixel of each reflected red light image may be associated with a location in the M×N matrix.

Consecutive transmit or emitting of IR light pulses and corresponding or simultaneous capture of the IR light reflections may also be performed. 1, 2, 3, 4, or more pulses of IR light and capture of IR light reflection data may be performed. Each pulse may include emitting IR light with a known power calibrated to several distances from the intraoral scanner exit window. Each IR light pulse illuminates for a known time period to control the energy amount of every wavelength. Each received frame of IR from this time slot is analyzed to isolate the area of interest for oxygen saturation calculations. Each area of interest may be divided to M×N matrix for localization of the tissue oxygen saturation. Each pixel of each reflected IR light image may be associated with a location in the M×N matrix.

If sufficient 3D data has been captured to generate a 3D model or a 3D model has been built, the process may proceed to block 1040. If not, the process may proceed to block 1010 for capture of additional 3D data, color data, and SpO2 data.

At block 1040, the SpO2 levels may be calculated and mapped to the 3D data or model. The red and IR reflected light data associated with the M×N matrix may be mapped to respective locations on the patient's detention, such as locations on the 3D model. In some embodiments, mapping the data may include an order in which the data is captured, such that the red and IR reflected light data is mapped based on the 3D scan frame or point cloud captured before or after the capture of the color data, such as immediately before or after the capture of the red and IR reflected light data. In some embodiments, each capture is time stamped and the red and IR reflected light data is mapped to the 3D data based on the time in which the red and IR reflected light data and 3D data is captured, such as mapping the red and IR reflected light data based on the 3D data captured within a period of time before and/or after the capture of the color data, such as within 10 ms, 20 ms, 30 ms, 50 ms, 75 ms, 100 ms, 200 ms, or 250 ms. red and IR reflected light data can be mapped to the 3D model to generate a color 3D model of the patient's detention.

The SpO2 levels may be calculated based on the mapped red and IR reflected light data. In calculating blood oxygen saturation based on light absorption characteristics of hemoglobin, there are two factors that are used to calculate SpO2, the AC or alternating component and the and DC or constant or offset component.

The AC component represents the pulsatile changes in blood oxygen saturation as a result of blood volume and movement changes that occur with each heartbeat. As the heart beats, blood is pumped into the arteries, causing a temporary increase in blood volume and oxygenated hemoglobin in the pulsatile component of the blood. The AC component is measured by the pulse oximeter as the difference between the maximum and minimum light absorbance during a single cardiac cycle.

The DC component represents the non-pulsatile blood volume, including both the oxygenated and deoxygenated hemoglobin in the arteries and veins. The DC component is measured by the pulse oximeter as the average light absorbance over time.

The ratio of the AC component to the DC component is used to calculate SpO2. This is because the AC component primarily reflects the oxygen saturation level of arterial blood, while the DC component reflects the total amount of blood in the tissue being measured. By comparing the ratio of the AC and DC components at the two different wavelengths of light (red and infrared), the pulse oximeter can estimate the oxygen saturation level of the arterial blood.

The ratio is called the modulation ratio and may be calculated using the AC and DC components of the red and infrared signals according to an equation, such as the R ratio equation discussed herein that has been calibrated based on empirical calibration, a set of measurements is taken at various oxygen saturation levels while the person being measured is still and not moving. The light source and detector of a reflective oxygen saturation sensor system is placed on or pointed at a finger, toe, earlobe, or gingiva. The person's oxygen saturation may be adjusted to different levels by changing the amount of oxygen in the air they breathe or by adjusting other variables that affect oxygen saturation.

The reference values obtained from the laboratory blood gas analyzer are then compared to the readings, such as the modulation ratio calculated from the data gathered by the light sensor or the reflective oxygen saturation sensor system. Any differences between the two are used to adjust the calibration of the reflective oxygen saturation sensor system, such as by using regression analysis to fit a curve to the data.

The calibration function is then stored in the reflective oxygen saturation sensor system memory and used to convert the instrument's sensor data, such as the red and IR data into an estimate of oxygen saturation.

In some embodiments, calibration may also include calibrating based on the distance the distal end of the intraoral scanner is from the gingiva. Because the distance can play a role in the intensity of illuminating light that is incited to the gingiva and the reflected light that is recorded by the sensor, the system maybe calibrated at multiple distances. The distance of the intraoral scanner from the gingiva may also be associated with each reading. The distance of the intraoral scanner (which may be determined from the 3D scan data) and calibration data may be used in determining the SpO2 levels for each location on the patient's gingiva.

Once calculated, the oxygen saturation mapping may be associated with a sub layer of the 3D scan data. Upon stitching of consecutives 3D scans, the oxygen saturation mapping layer may be stitched to generate a full 3D data layer of the 3D scanned tissues in the mouth for oxygen saturation values.

With non-uniformity results of SpO2 levels on the final model and\or within live measuring and over time of same area, the doctor may evaluate the quality of the patient oral blood flow.

After mapping the SpO2 data, the process may continue to block 1010 where the process is repeated until the patient's dentition is scanned.

Figure 11:
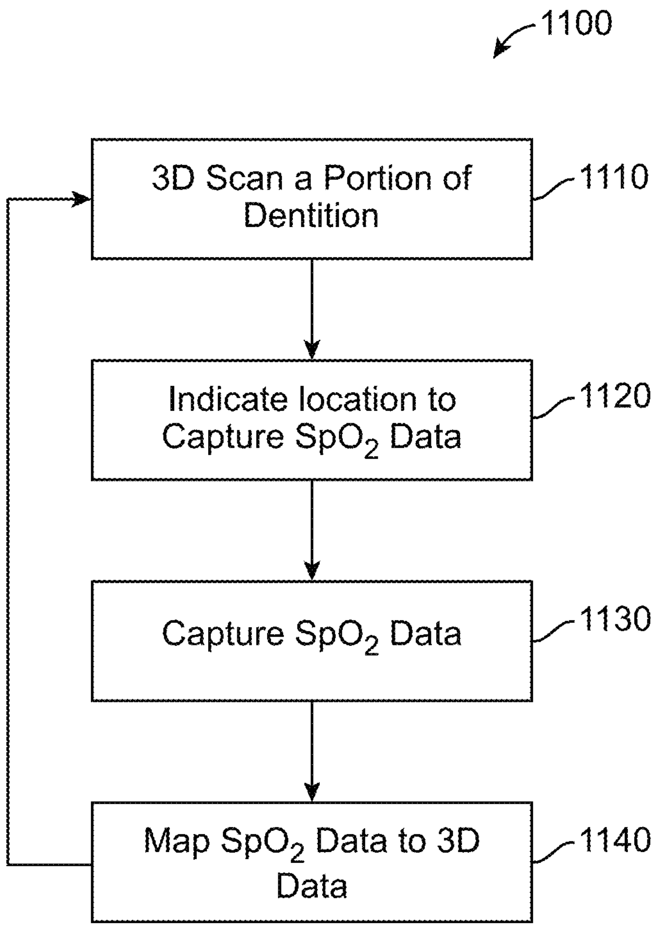
FIG. 11 shows a method of scanning and determining blood oxygen levels using an intraoral scanner, in accordance with some embodiments.

FIG. 11 depicts a method of scanning a patient's detention and using a contact method for measuring SpO2 levels. The process may start at block 1110. At block 1110, an intraoral scanner 120, which may include aspects of the probe 100 and/or probe 200 scans a patient's dentition, which may include the patient's teeth and gingiva. The 3D scanning process may include capturing point cloud data. During the scanning process, the scanner emits light, such as laser or structured light that bounces off the surface of the patient's dental tissues. The image sensor in the scanner measures aspects of the returning light, such as the focus, the time of flight, phase shift, or the image of the structured light to determine the distance between the scanner and the surface. This process is repeated at different locations and angles as the intraoral scanner is moved. The point cloud data may be stored for registration with additional point cloud data captured later.

In some embodiments, if a partial 3D model of previously scanned and registered point clouds exists, the captured point cloud data may be registered with the existing point cloud data or 3D model.

In some embodiments, the point clouds may be cleaned and/or filtered. After the point clouds are captured, they may contain noise, outliers, and other artifacts that can affect the accuracy of the 3D resulting 3D model. To clean and filter the point clouds, various algorithms are used, such as statistical outlier removal, smoothing, and hole filling. Statistical outlier removal involves identifying and removing points that are significantly different from the surrounding points based on their distance or intensity values. Smoothing involves averaging the values of neighboring points to reduce noise and create a smoother surface. Hole filling involves interpolating values for missing data or regions where the scanner was unable to capture data.

The point clouds may then be combined to create a 3D model of the patient's dentition through a process called registration. Registration involves aligning the point clouds so that they are in the correct position relative to each other. There are several techniques that can be used for registration, including iterative closest point (ICP), feature-based matching, and global registration. ICP involves iteratively minimizing the distance between corresponding points in the point clouds. Feature-based matching involves identifying distinctive features of the object or environment, such as edges or corners, and using these features to find correspondences between the point clouds. Global registration may include aligning the point clouds to a common coordinate system based on known reference points or markers.

When two point clouds are registered, they may be meshed to form a surface model. The mesh may be updated when each additional point cloud is registered to the model.

Color data may be captured. Color data, such as 2D color images, are captured as part of the scanning process. If the color data is captured early in the scanning process, such as before a 3D model has been generated, the color data may be stored for later mapping to a 3D model. The color data may be associated with a frame or multiple frames of captured 3D data, such as one or more point clouds. After sufficient point cloud data is captured to start building a 3D model of the patient's detention, the color data may be mapped to the 3D model based on the point cloud frame or frames to which it is associated. In some embodiments, associating may include an order in which the data is captured, such that the color data is mapped based on the 3D scan frame or point captured before or after the capture of the color data, such as immediately before or after the capture of the color data. In some embodiments, each capture is time stamped and the color data is mapped to the 3D data based on the time in which the color and 3D data is captured, such as mapping the color data based on the 3D data captured within a period of time before and/or after the capture of the color data, such as within 10 ms, 20 ms, 30 ms, 50 ms, 75 ms, 100 ms, 200 ms, or 250 ms. The color data can be mapped to the 3D model to generate a color 3D model of the patient's detention.

A 3D model of a portion of the patient's detention may be generated based on the 3D scan data. In some embodiments, the 3D model may also include the color data.

At block 1120, a location for measuring capturing SpO2 data may be indicated on the 3D model. The indication may be a highlighted location, a perimeter shape such as a circle or square that surrounds the location, an arrow pointing to the location, or other indication.

At block 1130, SpO2 data is captured using a contact method. In some embodiments, the intraoral scanner may contact the gingiva of the patient at the indicated location and held in place to determine the SpO2 using a contact method and system, such as described with respect to FIG. 2B. The SpO2 measurement may be conducted over a time period, such as at least 1, 2, 3, 4, 5, or more seconds or until the system determines that sufficient SpO2 data has been captured. Then, the SpO2 level may be determined based on the red and IR reflected light data captured while the intraoral scanner contacts the gingiva at the indicated location. In calculating blood oxygen saturation based on light absorption characteristics of hemoglobin, there are two factors that are used to calculate SpO2, the AC or alternating component and the and DC or constant or offset component, as discussed herein.

At block 1140, the SpO2 data may be mapped to the 3D data. For example, the location of the SpO2 measurement may be recorded, such as on the indicated location of the 3D model.

The process may then proceed back to block 1110 and repeated, such as until the dentition is scanned.

Figure 12:
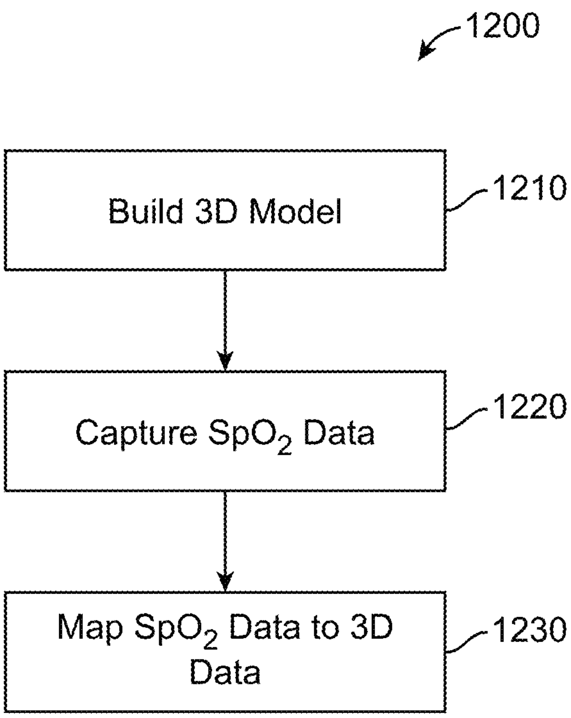
FIG. 12 shows a method of scanning and determining blood oxygen levels, in accordance with some embodiments.

FIG. 12 depicts a method 1200 of capturing and mapping SpO2 data to an existing 3D model. At block 1210 a 3D model of the patients detention may be built or otherwise generated as discussed herein. In some movements, the model may be received, such as by an intraoral scanning system.

At block 1220, SpO2 data may be captured. Consecutive transmit or emitting of red light pulses and corresponding or simultaneous capture of the red light reflections may be performed. 1, 2, 3, 4, or more pulses of red light and capture of red light reflection data may be performed. Each pulse may include emitting red light with a known power calibrated to several distances from the intraoral scanner exit window. Each red light pulse illuminates for a known time period to control the energy amount of every wavelength. Each received frame of red from this time slot is analyzed to isolate the area of interest for oxygen saturation calculations. Each area of interest may be divided to M×N matrix for localization of the tissue oxygen saturation. Each pixel of each reflected red light image may be associated with a location in the M×N matrix.

Consecutive transmit or emitting of IR light pulses and corresponding or simultaneous capture of the IR light reflections may also be performed. 1, 2, 3, 4, or more pulses of IR light and capture of IR light reflection data may be performed. Each pulse may include emitting IR light with a known power calibrated to several distances from the intraoral scanner exit window. Each IR light pulse illuminates for a known time period to control the energy amount of every wavelength. Each received frame of IR from this time slot is analyzed to isolate the area of interest for oxygen saturation calculations. Each area of interest may be divided to M×N matrix for localization of the tissue oxygen saturation. Each pixel of each reflected IR light image may be associated with a location in the M×N matrix.

In some embodiments, at block 1220, 3D data may be captured and mapped to the 3D model in order to determine the location of the capture of the SpO2 data.

At block 1230, the SpO2 levels may be calculated and mapped to the 3D data or model. The red and IR reflected light data associated with the M×N matrix may be mapped to respective locations on the patient's detention, such as locations on the 3D model, such as based on the 3D data captured at block 1220.

The SpO2 levels may be calculated based on the mapped red and IR reflected light data. In calculating blood oxygen saturation based on light absorption characteristics of hemoglobin, there are two factors that are used to calculate SpO2, the AC or alternating component and the and DC or constant or offset component.

The AC component represents the pulsatile changes in blood oxygen saturation as a result of blood volume and movement changes that occur with each heartbeat. As the heart beats, blood is pumped into the arteries, causing a temporary increase in blood volume and oxygenated hemoglobin in the pulsatile component of the blood. The AC component is measured by the pulse oximeter as the difference between the maximum and minimum light absorbance during a single cardiac cycle.

The DC component represents the non-pulsatile blood volume, including both the oxygenated and deoxygenated hemoglobin in the arteries and veins. The DC component is measured by the pulse oximeter as the average light absorbance over time.

The ratio of the AC component to the DC component is used to calculate SpO2. This is because the AC component primarily reflects the oxygen saturation level of arterial blood, while the DC component reflects the total amount of blood in the tissue being measured. By comparing the ratio of the AC and DC components at the two different wavelengths of light (red and infrared), the pulse oximeter can estimate the oxygen saturation level of the arterial blood.

The ratio is called the modulation ratio and may be calculated using the AC and DC components of the red and infrared signals according to an equation, such as the R ratio equation discussed herein that has been calibrated based on empirical calibration, as discussed herein.

Once calculated, the oxygen saturation mapping may be associated with a sub layer of the 3D scan data. Upon stitching of consecutives 3D scans, the oxygen saturation mapping layer may be stitched to generate a full 3D data layer of the 3D scanned tissues in the mouth for oxygen saturation values.

Computing System

FIG. 12 is a block diagram of an example computing system 1310 capable of implementing one or more of the embodiments described and/or illustrated herein. For example, all or a portion of computing system 1310 may perform and/or be a means for performing, either alone or in combination with other elements, one or more of the steps described herein (such as one or more of the steps illustrated in FIGS. 1-10. All or a portion of computing system 1310 may also perform and/or be a means for performing any other steps, methods, or processes described and/or illustrated herein.

Computing system 1310 broadly represents any single or multi-processor computing device or system capable of executing computer-readable instructions. Examples of computing system 1310 include, without limitation, workstations, laptops, client-side terminals, servers, distributed computing systems, handheld devices, or any other computing system or device. In its most basic configuration, computing system 1310 may include at least one processor 1314 and a system memory 1316.

Processor 1314 generally represents any type or form of physical processing unit (e.g., a hardware-implemented central processing unit) capable of processing data or interpreting and executing instructions. In certain embodiments, processor 1314 may receive instructions from a software application or module. These instructions may cause processor 1314 to perform the functions of one or more of the example embodiments described and/or illustrated herein.

System memory 1316 generally represents any type or form of volatile or non-volatile storage device or medium capable of storing data and/or other computer-readable instructions. Examples of system memory 1316 include, without limitation, Random Access Memory (RAM), Read Only Memory (ROM), flash memory, or any other suitable memory device. Although not required, in certain embodiments computing system 1310 may include both a volatile memory unit (such as, for example, system memory 1316) and a non-volatile storage device (such as, for example, primary storage device 1332, as described in detail below).

In some examples, system memory 1316 may store and/or load an operating system 1340 for execution by processor 1314. In one example, operating system 1340 may include and/or represent software that manages computer hardware and software resources and/or provides common services to computer programs and/or applications on computing system 1310. Examples of operating system 1340 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In certain embodiments, example computing system 1310 may also include one or more components or elements in addition to processor 1314 and system memory 1316. For example, as illustrated in FIG. 12, computing system 1310 may include a memory controller 1318, an Input/Output (I/O) controller 1320, and a communication interface 1322, each of which may be interconnected via a communication infrastructure 1312. Communication infrastructure 1312 generally represents any type or form of infrastructure capable of facilitating communication between one or more components of a computing device. Examples of communication infrastructure 1312 include, without limitation, a communication bus (such as an Industry Standard Architecture (ISA), Peripheral Component Interconnect (PCI), PCI Express (PCIe), or similar bus) and a network.

Memory controller 1318 generally represents any type or form of device capable of handling memory or data or controlling communication between one or more components of computing system 1310. For example, in certain embodiments memory controller 1318 may control communication between processor 1314, system memory 1316, and I/O controller 1320 via communication infrastructure 1312.

I/O controller 1320 generally represents any type or form of module capable of coordinating and/or controlling the input and output functions of a computing device. For example, in certain embodiments I/O controller 1320 may control or facilitate transfer of data between one or more elements of computing system 1310, such as processor 1314, system memory 1316, communication interface 1322, display adapter 1326, input interface 1330, and storage interface 1334.

As illustrated in FIG. 12, computing system 1310 may also include at least one display device 1324 coupled to I/O controller 1320 via a display adapter 1326. Display device 1324 generally represents any type or form of device capable of visually displaying information forwarded by display adapter 1326. Similarly, display adapter 1326 generally represents any type or form of device configured to forward graphics, text, and other data from communication infrastructure 1312 (or from a frame buffer, as known in the art) for display on display device 1324.

As illustrated in FIG. 12, example computing system 1310 may also include at least one input device 1328 coupled to I/O controller 1320 via an input interface 1330. Input device 1328 generally represents any type or form of input device capable of providing input, either computer or human generated, to example computing system 1310. Examples of input device 1328 include, without limitation, a keyboard, a pointing device, a speech recognition device, variations or combinations of one or more of the same, and/or any other input device.

Additionally or alternatively, example computing system 1310 may include additional I/O devices. For example, example computing system 1310 may include I/O device 1336. In this example, I/O device 1336 may include and/or represent a user interface that facilitates human interaction with computing system 1310. Examples of I/O device 1336 include, without limitation, a computer mouse, a keyboard, a monitor, a printer, a modem, a camera, a scanner, a microphone, a touchscreen device, variations or combinations of one or more of the same, and/or any other I/O device.

Communication interface 1322 broadly represents any type or form of communication device or adapter capable of facilitating communication between example computing system 1310 and one or more additional devices. For example, in certain embodiments communication interface 1322 may facilitate communication between computing system 1310 and a private or public network including additional computing systems. Examples of communication interface 1322 include, without limitation, a wired network interface (such as a network interface card), a wireless network interface (such as a wireless network interface card), a modem, and any other suitable interface. In at least one embodiment, communication interface 1322 may provide a direct connection to a remote server via a direct link to a network, such as the Internet. Communication interface 1322 may also indirectly provide such a connection through, for example, a local area network (such as an Ethernet network), a personal area network, a telephone or cable network, a cellular telephone connection, a satellite data connection, or any other suitable connection.

In certain embodiments, communication interface 1322 may also represent a host adapter configured to facilitate communication between computing system 1310 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 1322 may also allow computing system 1310 to engage in distributed or remote computing. For example, communication interface 1322 may receive instructions from a remote device or send instructions to a remote device for execution.

In some examples, system memory 1316 may store and/or load a network communication program 1338 for execution by processor 1314. In one example, network communication program 1338 may include and/or represent software that enables computing system 1310 to establish a network connection 1342 with another computing system (not illustrated in FIG. 12) and/or communicate with the other computing system by way of communication interface 1322. In this example, network communication program 1338 may direct the flow of outgoing traffic that is sent to the other computing system via network connection 1342. Additionally or alternatively, network communication program 1338 may direct the processing of incoming traffic that is received from the other computing system via network connection 1342 in connection with processor 1314.

Although not illustrated in this way in FIG. 12, network communication program 1338 may alternatively be stored and/or loaded in communication interface 1322. For example, network communication program 1338 may include and/or represent at least a portion of software and/or firmware that is executed by a processor and/or Application Specific Integrated Circuit (ASIC) incorporated in communication interface 1322.

As illustrated in FIG. 12, example computing system 1310 may also include a primary storage device 1332 and a backup storage device 1333 coupled to communication infrastructure 1312 via a storage interface 1334. Storage devices 1332 and 1333 generally represent any type or form of storage device or medium capable of storing data and/or other computer-readable instructions. For example, storage devices 1332 and 1333 may be a magnetic disk drive (e.g., a so-called hard drive), a solid state drive, a floppy disk drive, a magnetic tape drive, an optical disk drive, a flash drive, or the like. Storage interface 1334 generally represents any type or form of interface or device for transferring data between storage devices 1332 and 1333 and other components of computing system 1310.

In certain embodiments, storage devices 1332 and 1333 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 1332 and 1333 may also include other similar structures or devices for allowing computer software, data, or other computer-readable instructions to be loaded into computing system 1310. For example, storage devices 1332 and 1333 may be configured to read and write software, data, or other computer-readable information. Storage devices 1332 and 1333 may also be a part of computing system 1310 or may be a separate device accessed through other interface systems.

Many other devices or subsystems may be connected to computing system 1310. Conversely, all of the components and devices illustrated in FIG. 12 need not be present to practice the embodiments described and/or illustrated herein. The devices and subsystems referenced above may also be interconnected in different ways from that shown in FIG. 12. Computing system 1310 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium.

The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 1310. All or a portion of the computer program stored on the computer-readable medium may then be stored in system memory 1316 and/or various portions of storage devices 1332 and 1333. When executed by processor 1314, a computer program loaded into computing system 1310 may cause processor 1314 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 1310 may be configured as an Application Specific Integrated Circuit (ASIC) adapted to implement one or more of the example embodiments disclosed herein.

Figure 13:
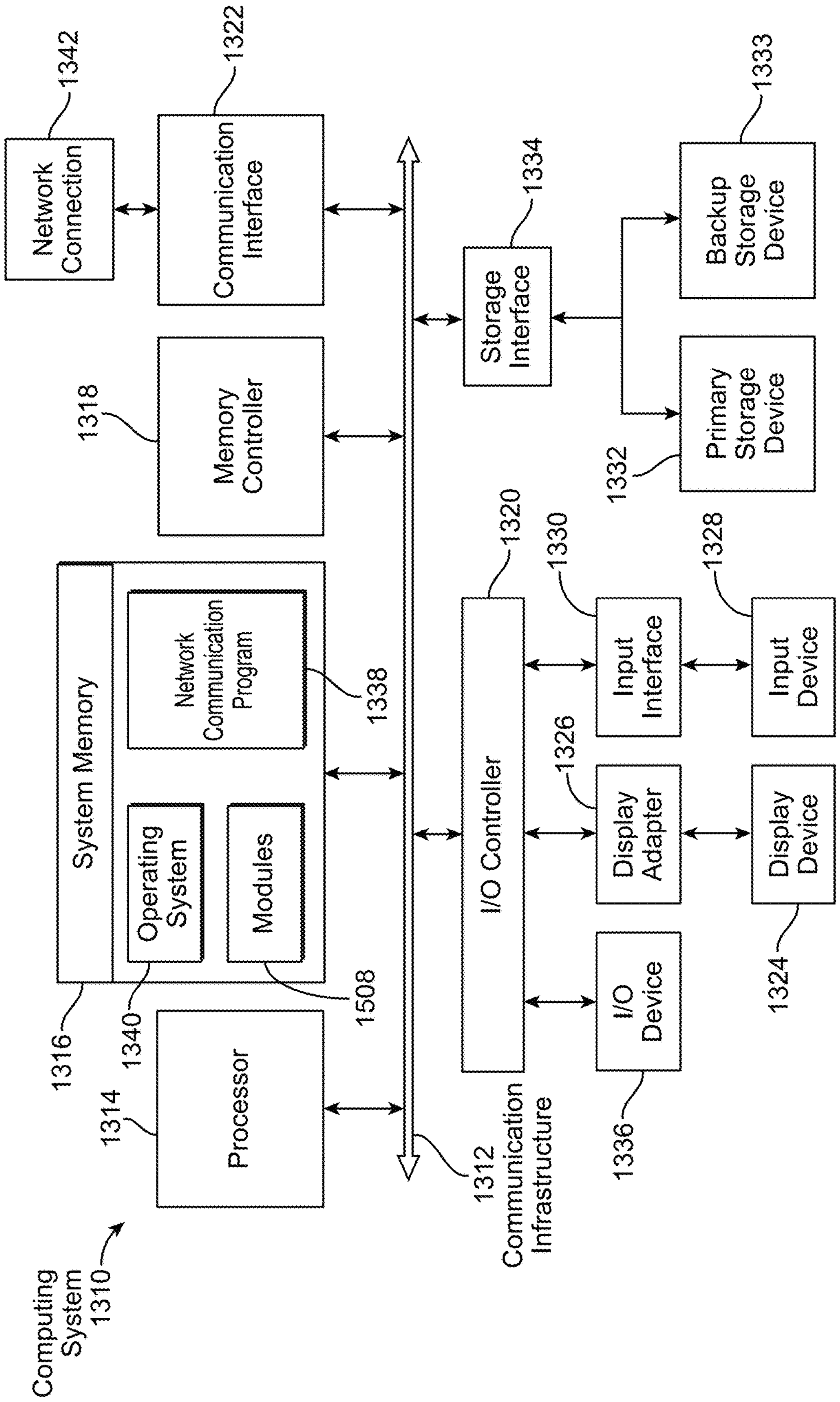
FIG. 13 shows a block diagram of an example computing system capable of implementing one or more embodiments described and/or illustrated herein, in accordance with embodiments.
Figure 14:
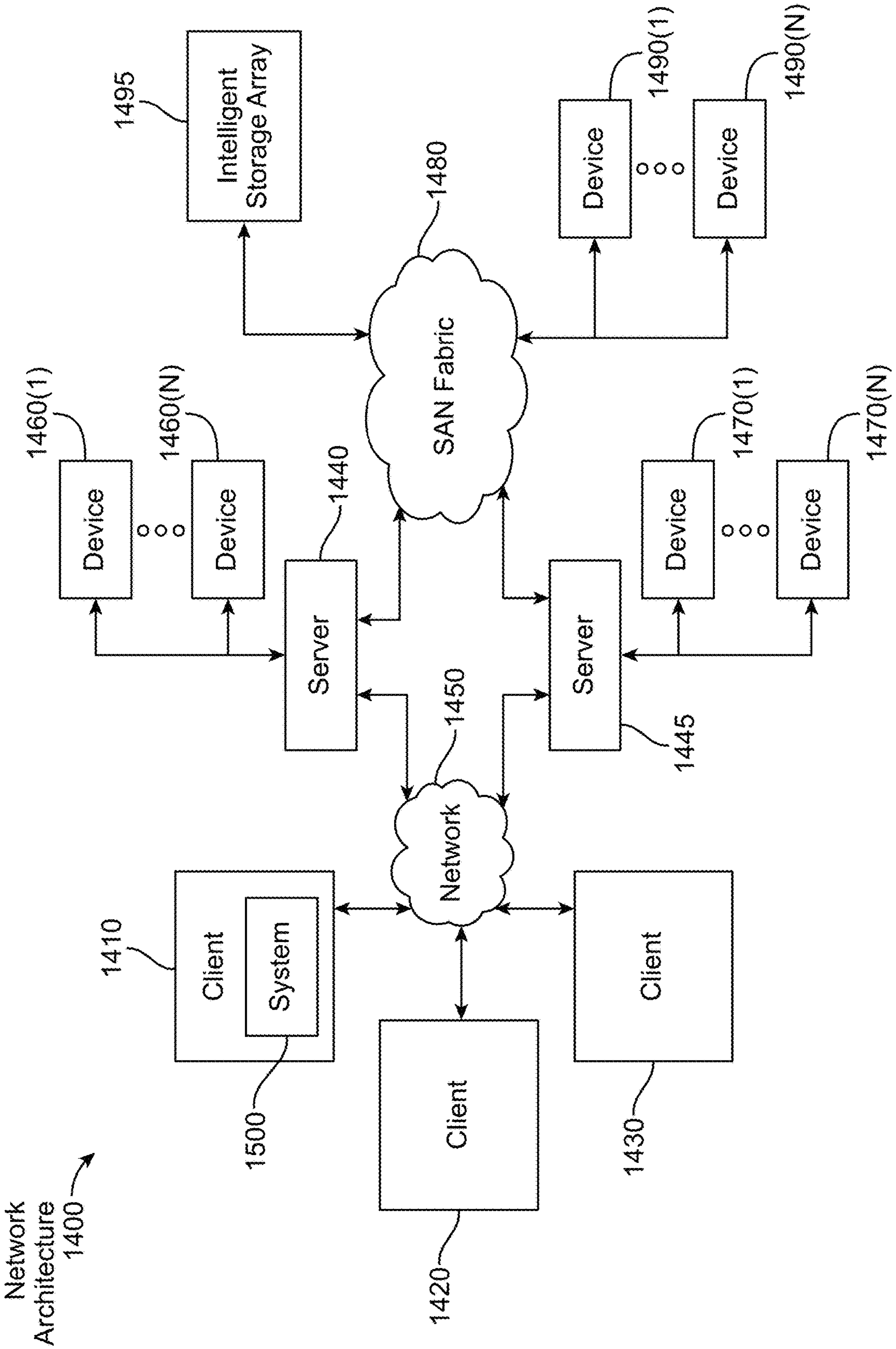
FIG. 14 shows a block diagram of an example computing network capable of implementing one or more of the embodiments described and/or illustrated herein, in accordance with embodiments.

FIG. 13 is a block diagram of an example network architecture 1400 in which client systems 1410, 1420, and 1430 and servers 1440 and 1445 may be coupled to a network 1450. As detailed above, all or a portion of network architecture 1400 may perform and/or be a means for performing, either alone or in combination with other elements, one or more of the steps disclosed herein (such as one or more of the steps illustrated in FIG. 4-11). All or a portion of network architecture 1400 may also be used to perform and/or be a means for performing other steps and features set forth in the instant disclosure.

Client systems 1410, 1420, and 1430 generally represent any type or form of computing device or system, such as example computing system 1310 in FIG. 12. Similarly, servers 1440 and 1445 generally represent computing devices or systems, such as application servers or database servers, configured to provide various database services and/or run certain software applications. Network 1450 generally represents any telecommunication or computer network including, for example, an intranet, a WAN, a LAN, a PAN, or the Internet. In one example, client systems 1410, 1420, and/or 1430 and/or servers 1440 and/or 1445 may include all or a portion of system 500 from FIG. 5.

As illustrated in FIG. 13, one or more storage devices 1460(1)-(N) may be directly attached to server 1440. Similarly, one or more storage devices 1470(1)-(N) may be directly attached to server 1445. Storage devices 1460(1)-(N) and storage devices 1470(1)-(N) generally represent any type or form of storage device or medium capable of storing data and/or other computer-readable instructions. In certain embodiments, storage devices 1460(1)-(N) and storage devices 1470(1)-(N) may represent Network-Attached Storage (NAS) devices configured to communicate with servers 1440 and 1445 using various protocols, such as Network File System (NFS), Server Message Block (SMB), or Common Internet File System (CIFS).

Servers 1440 and 1445 may also be connected to a Storage Area Network (SAN) fabric 1480. SAN fabric 1480 generally represents any type or form of computer network or architecture capable of facilitating communication between a plurality of storage devices. SAN fabric 1480 may facilitate communication between servers 1440 and 1445 and a plurality of storage devices 1490(1)-(N) and/or an intelligent storage array 1495. SAN fabric 1480 may also facilitate, via network 1450 and servers 1440 and 1445, communication between client systems 1410, 1420, and 1430 and storage devices 1490(1)-(N) and/or intelligent storage array 1495 in such a manner that devices 1490(1)-(N) and array 1495 appear as locally attached devices to client systems 1410, 1420, and 1430. As with storage devices 1460(1)-(N) and storage devices 1470(1)-(N), storage devices 1490(1)-(N) and intelligent storage array 1495 generally represent any type or form of storage device or medium capable of storing data and/or other computer-readable instructions.

In certain embodiments, and with reference to example computing system 1310 of FIG. 12, a communication interface, such as communication interface 1322 in FIG. 12, may be used to provide connectivity between each client system 1410, 1420, and 1430 and network 1450. Client systems 1410, 1420, and 1430 may be able to access information on server 1440 or 1445 using, for example, a web browser or other client software. Such software may allow client systems 1410, 1420, and 1430 to access data hosted by server 1440, server 1445, storage devices 1460(1)-(N), storage devices 1470(1)-(N), storage devices 1490(1)-(N), or intelligent storage array 1495. Although FIG. 12 depicts the use of a network (such as the Internet) for exchanging data, the embodiments described and/or illustrated herein are not limited to the Internet or any particular network-based environment.

In at least one embodiment, all or a portion of one or more of the example embodiments disclosed herein may be encoded as a computer program and loaded onto and executed by server 1440, server 1445, storage devices 1460(1)-(N), storage devices 1470(1)-(N), storage devices 1490(1)-(N), intelligent storage array 1495, or any combination thereof. All or a portion of one or more of the example embodiments disclosed herein may also be encoded as a computer program, stored in server 1440, run by server 1445, and distributed to client systems 1410, 1420, and 1430 over network 1450.

As detailed above, computing system 1310 and/or one or more components of network architecture 1400 may perform and/or be a means for performing, either alone or in combination with other elements, one or more steps of an example method for virtual care.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of the example systems disclosed herein may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various embodiments, all or a portion of example systems disclosed herein may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various embodiments, all or a portion of example systems disclosed herein may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example systems disclosed herein may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of example systems disclosed herein may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some embodiments, all or a portion of example systems disclosed herein may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A system of generating a blood oxygen saturation map of a patient's gingiva, the system comprising: a processor and memory comprising instructions that when executed by the processor cause the system to: generate 3D scan data of a first portion of a dentition of a patient including a first portion of a gingiva of the patient; capture red light data of reflected red light from the first portion of the gingiva of the patient with an image sensor while the first portion of the gingiva of the patient is illuminated with red light; capture infrared light data of reflected infrared light from the first portion of the gingiva of the patient with an image sensor while the first portion of the gingiva of the patient is illuminated with infrared light; determine a blood oxygen saturation of the first portion of the gingiva of the patient based on the red light data and the infrared light data; and map the blood oxygen saturation of the first portion of the gingiva of the patient to the 3D scan data.

Clause 2. The system of clause 1, wherein the memory further comprises instructions that when executed by the processor further cause the system to: generate a 3D model of the dentition of the patient, including the first portion of the gingiva of the patient, based on the 3D scan data.

Clause 3. The system of clause 2, wherein the instructions that when executed cause the system to map the blood oxygen saturation of the first portion of the gingiva of the patient to the 3D scan data include instructions to map the blood oxygen saturation of the first portion of the gingiva of the patient to the 3D model.

Clause 4. The system of clause 3, wherein the memory further comprises instructions that when executed by the processor further cause the system to: display the 3D model of the dentition of the patient with the mapped blood oxygen saturation data.

Clause 5. The system of clause 4, wherein the instructions that when executed cause the system to display the 3D model of the dentition of the patient with the mapped blood oxygen saturation data include instructions to indicate a blood oxygen saturation percentage at a location on the model.

Clause 6. The system of clause 5, wherein the instructions that when executed cause the system to display the 3D model of the dentition of the patient with the mapped blood oxygen saturation data include instructions to indicate the blood oxygen saturation percentage at the location on the model includes modifying a color of the model at the location based on the blood oxygen saturation percentage.

Clause 7. The system of clause 6, wherein modifying the color includes applying a hatch pattern to the location on the model.

Clause 8. The system of clause 6, wherein modifying the color includes a first modification to the color based on a first blood oxygen saturation percentage threshold or range.

Clause 9. The system of clause 8, wherein modifying the color includes a second modification to the color based on a second blood oxygen saturation percentage threshold or range.

Clause 10. The system of clause 1, further comprising: capturing color data of the dentition of the patient using an intraoral scanner, and mapping the color data to the 3D data, wherein displaying the 3D model of the dentition of the patient with the mapped blood oxygen saturation includes indicating a blood oxygen saturation percentage at a location on the 3D data by modifying the mapped color data based on the blood oxygen saturation percentage.

Clause 11. A system of generating a blood oxygen saturation map of a patient's gingiva, the system comprising: an intraoral scanner; a display; a processor; and memory comprising instructions that when executed by the processor cause the system to: generate, using the intraoral scanner, 3D scan data of a first portion of a dentition of a patient including a first portion of a gingiva of the patient; generate, using the intraoral scanner, blood oxygen saturation data for the first portion of the dentition of the patient including the first portion of the gingiva of the patient; generate a 3D model of the dentition of the patient, including the first portion of the gingiva of the patient, based on the 3D scan data; determine a blood oxygen saturation of the first portion of the gingiva of the patient based on the blood oxygen saturation data; map the blood oxygen saturation of the first portion of the gingiva of the patient to the 3D model; and display, on the display, the 3D model of the dentition of the patient with the mapped blood oxygen saturation data.

Clause 12. The system of clause 11, wherein: displaying the 3D model of the dentition of the patient with the mapped blood oxygen saturation data includes indicating a blood oxygen saturation percentage at a location on the model.

Clause 13. The system of clause 12, wherein: indicating a blood oxygen saturation percentage at the location on the model includes modifying a color of the model at the location.

Clause 14. The system of clause 11, the memory comprising instructions that when executed by the processor further cause the system to: capture color data of the dentition of the patient using an intraoral scanner, and map the color data to the 3D data before mapping the blood oxygen saturation data to the 3D data.

Clause 15. The system of clause 14, wherein the feedback includes modifying the color data at the locations based on the blood oxygen saturation data.

Clause 16. A system of generating a blood oxygen saturation map of a patient's gingiva, the system comprising: an intraoral scanner; a display; a processor; and memory comprising instructions that when executed by the processor cause the system to: generating, using the intraoral scanner, 3D scan data of a first portion of a dentition of a patient including a first portion of a gingiva of the patient; generating, using the intraoral scanner, blood oxygen saturation data for the first portion of the dentition of the patient including the first portion of the gingiva of the patient; mapping the blood oxygen saturation data of the first portion of the gingiva of the patient to the 3D scan data; and displaying, on the display, the 3D model of the dentition of the patient with feedback indicating locations of blood oxygen saturation below a threshold.

Clause 17. The system of clause 16, the memory comprising instructions that when executed by the processor further cause the system to: receive the blood oxygen threshold via user input.

Clause 18. The system of clause 16, wherein the feedback includes highlighting the locations.

Clause 19. The system of clause 16, wherein the feedback includes coloring the locations based on the blood oxygen saturation data.

Clause 20. The system of clause 16, wherein the feedback indicating locations of blood oxygen saturation below a threshold is configured to occur without feedback to second location that are not the locations of blood oxygen saturation below a threshold.

Clause 21. A method of generating a blood oxygen saturation map of a patient's gingiva using an intraoral scanner, the method comprising: generating 3D scan data of a first portion of a dentition of a patient including a first portion of a gingiva of the patient; capturing red light data of reflected red light from the first portion of the gingiva of the patient with an image sensor while the first portion of the gingiva of the patient is illuminated with red light; capturing infrared light data of reflected infrared light from the first portion of the gingiva of the patient with an image sensor while the first portion of the gingiva of the patient is illuminated with infrared light; determining a blood oxygen saturation of the first portion of the gingiva of the patient based on the red light data and the infrared light data; and mapping the blood oxygen saturation of the first portion of the gingiva of the patient to the 3D scan data.

Clause 22. The method of clause 21, further comprising: generating a 3D model of the dentition of the patient, including the first portion of the gingiva of the patient, based on the 3D scan data.

Clause 23. The method of clause 22, wherein mapping the blood oxygen saturation of the first portion of the gingiva of the patient to the 3D scan data including mapping the blood oxygen saturation of the first portion of the gingiva of the patient to the 3D model.

Clause 24. The method of clause 23, further comprising: displaying the 3D model of the dentition of the patient with the mapped blood oxygen saturation data.

Clause 25. The method of clause 24, wherein: displaying the 3D model of the dentition of the patient with the mapped blood oxygen saturation data includes indicating a blood oxygen saturation percentage at a location on the model.

Clause 26. The method of clause 25, wherein: displaying the 3D model of the dentition of the patient with the mapped blood oxygen saturation data includes indicating the blood oxygen saturation percentage at the location on the model includes modifying a color of the model at the location based on the blood oxygen saturation percentage.

Clause 27. The method of clause 26, wherein modifying the color includes apply a hatch pattern to the location on the model.

Clause 28. The method of clause 26, wherein modifying the color includes a first modification to the color based on a first blood oxygen saturation percentage threshold or range.

Clause 29. The method of clause 28, wherein modifying the color includes a second modification to the color based on a second blood oxygen saturation percentage threshold or range.

Clause 30. The method of clause 21, wherein: capturing red light data of reflected red light from the first portion of the gingiva of the patient with an image sensor while the first portion of the gingiva of the patient is illuminated with red light includes capturing a plurality of red light data of reflected red light from the first portion of the gingiva of the patient with an image sensor while the first portion of the gingiva of the patient is illuminated a plurality of times with red light.

Clause 31. The method of clause 30, wherein: capturing infrared light data of reflected infrared light from the first portion of the gingiva of the patient with an image sensor while the first portion of the gingiva of the patient is illuminated with infrared light includes capturing a plurality of infrared light data of reflected infrared light from the first portion of the gingiva of the patient with an image sensor while the first portion of the gingiva of the patient is illuminated a plurality of times with infrared light.

Clause 32. The method of clause 31, wherein: determining the blood oxygen saturation of the first portion of the gingiva of the patient based on the red light data and the infrared light data includes determining the blood oxygen saturation of the first portion of the patient's gingiva of the patient on the plurality of red light data and the plurality of infrared light data.

Clause 33. The method of clause 32, wherein the plurality of red light data and the plurality of infrared light data is captured over a time period of at least 1 second.

Clause 34. The method of clause 32, wherein the plurality of red light data and the plurality of infrared light data is captured over a time period of at least 4 seconds.

Clause 35. The method of clause 21, further comprising: illuminating the first portion of the gingiva of the patient with infrared light.

Clause 36. The method of clause 21, further comprising: illuminating the first portion of the gingiva of the patient with red light.

Clause 37. The method of clause 21, wherein: the red light is light with a wavelength between 650 nm and 730 nm.

Clause 38. The method of clause 21, wherein: the infrared light is light with a wavelength between 850 nm and 950 nm.

Clause 39. The method of clause 21, wherein: the red light is light with a wavelength between 690 nm and 710 nm.

Clause 40. The method of clause 21, wherein: the infrared light is light with a wavelength between 890 nm and 910 nm.

Clause 41. The method of clause 21, further comprising: contacting the gingiva of the patient at a location on the first portion of the gingiva of the patient during the capturing red light data of reflected red light from the first portion of the gingiva of the patient with an image sensor while the first portion of the gingiva of the patient is illuminated with red light and the capturing infrared light data of reflected infrared light from the first portion of the gingiva of the patient with an image sensor while the first portion of the gingiva of the patient is illuminated with infrared light.

Clause 42. The method of clause 41, wherein a light sensor captures the red light and the infrared light, the light sensors being different than the image sensor.

Clause 43. The method of clause 32, wherein determining the blood oxygen saturation of the first portion of the gingiva of the patient based on the red light data and the infrared light data includes determining a AC component of light absorption characteristics of hemoglobin of the patient based on the plurality of red light data and the plurality of infrared light data.

Clause 44. The method of clause 43, wherein determining the blood oxygen saturation of the first portion of the gingiva of the patient based on the red light data and the infrared light data includes determining a DC component of light absorption characteristics of hemoglobin of the patient based on the plurality of red light data and the plurality of infrared light data.

Clause 45. The method of clause 44, wherein: determining the blood oxygen saturation of the first portion of the patient's gingiva of the patient on the red light data and the infrared light data includes determining an R ratio based on the AC component and the DC component, and wherein determining a SpO2 percentage based on the R ratio and a calibration curve.

Clause 46. The method of clause 21, further comprising: capturing color data of the dentition of the patient using an intraoral scanner, and mapping the color data to the 3D data.

Clause 47. The method of clause 46, wherein: displaying the 3D model of the dentition of the patient with the mapped blood oxygen saturation includes indicating a blood oxygen saturation percentage at a location on the 3D data.

Clause 48. The method of clause 47, wherein: displaying the 3D model of the dentition of the patient with the mapped blood oxygen saturation includes indicating the blood oxygen saturation percentage at the location on the 3D data includes modifying the mapped color data based on the blood oxygen saturation percentage.

Clause 49. The method of clause 48, wherein modifying the mapped color data includes changing the color of the mapped color data.

Clause 50. The method of clause 48, wherein modifying the mapped color data includes changing applying a hatch pattern to the mapped color data.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A system of generating a blood oxygen saturation map of a patient's gingiva, the system comprising:

a processor and memory comprising instructions that when executed by the processor cause the system to:

generate 3D scan data of a first portion of a dentition of a patient including a first portion of a gingiva of the patient;

capture red light data of reflected red light from the first portion of the gingiva of the patient with an image sensor while the first portion of the gingiva of the patient is illuminated with red light;

capture infrared light data of reflected infrared light from the first portion of the gingiva of the patient with the image sensor while the first portion of the gingiva of the patient is illuminated with infrared light;

determine a blood oxygen saturation of the first portion of the gingiva of the patient based on the red light data and the infrared light data;

map the blood oxygen saturation of the first portion of the gingiva of the patient to the 3D scan data; and display the 3D scan data modified with an indication associated with the blood oxygen saturation of the first portion of the gingiva mapped to the 3D scan data.

2. The system of claim 1, wherein the memory further comprises instructions that when executed by the processor further cause the system to:

generate a 3D model of the dentition of the patient, including the first portion of the gingiva of the patient, based on the 3D scan data.

3. The system of claim 2, wherein the instructions that when executed cause the system to map the blood oxygen saturation of the first portion of the gingiva of the patient to the 3D scan data include instructions to map the blood oxygen saturation of the first portion of the gingiva of the patient to the 3D model.

4. The system of claim 3, wherein the memory further comprises instructions that when executed by the processor further cause the system to:

display the 3D model of the dentition of the patient with the mapped blood oxygen saturation data.

5. The system of claim 4, wherein the instructions that when executed cause the system to display the 3D model of the dentition of the patient with the mapped blood oxygen saturation data include instructions to indicate a blood oxygen saturation percentage at a location on the 3D model.

6. The system of claim 5, wherein the instructions that when executed cause the system to indicate the blood oxygen saturation percentage at the location on the 3D model include instructions to modify a color of the 3D model at the location based on the blood oxygen saturation percentage.

7. The system of claim 6, wherein modifying the color includes applying a hatch pattern to the location on the 3D model.

8. The system of claim 6, wherein modifying the color includes a first modification to the color based on a first blood oxygen saturation percentage threshold or range.

9. The system of claim 8, wherein modifying the color includes a second modification to the color based on a second blood oxygen saturation percentage threshold or range.

10. The system of claim 1, wherein the memory further comprises instructions that when executed, cause the system to:

capture color data of the dentition of the patient using an intraoral scanner, map the color data to the 3D scan data, and wherein the instructions that display the 3D scan data of the dentition of the patient include instructions to indicate a blood oxygen saturation percentage at a location on the 3D scan data by modifying the mapped color data based on the blood oxygen saturation percentage.

11. A system of generating a blood oxygen saturation map of a patient's gingiva, the system comprising:

an intraoral scanner;

a display;

a processor; and memory comprising instructions that when executed by the processor cause the system to:

generate, using the intraoral scanner, 3D scan data of a first portion of a dentition of a patient including a first portion of a gingiva of the patient;

generate, using the intraoral scanner, blood oxygen saturation data for the first portion of the dentition of the patient including the first portion of the gingiva of the patient;

generate a 3D model of the dentition of the patient, including the first portion of the gingiva of the patient, based on the 3D scan data;

determine a blood oxygen saturation of the first portion of the gingiva of the patient based on the blood oxygen saturation data;

map the blood oxygen saturation of the first portion of the gingiva of the patient to the 3D model; and display, on the display, the 3D model modified with an indication associated with the blood oxygen saturation of the first portion of the gingiva mapped to the 3D model.

12. The system of claim 11, wherein:

displaying the 3D model of the dentition of the patient with the mapped blood oxygen saturation data includes indicating a blood oxygen saturation percentage at a location on the 3D model.

13. The system of claim 12, wherein:

indicating a blood oxygen saturation percentage at the location on the model includes modifying a color of the 3D model at the location.

14. The system of claim 11, wherein the memory comprising instructions that when executed by the processor further cause the system to:

capture color data of the dentition of the patient using the intraoral scanner, and map the color data to the 3D scan data before mapping the blood oxygen saturation data to the 3D scan data.

15. The system of claim 14, wherein the memory comprising instructions that when executed by the processor further comprises instructions that cause the system to modify the color data at a locations based on the blood oxygen saturation data to provide feedback indicating blood oxygen saturation below a threshold.

16. A system of generating a blood oxygen saturation map of a patient's gingiva, the system comprising:

an intraoral scanner;

a display;

a processor; and memory comprising instructions that when executed by the processor cause the system to:

generate, using the intraoral scanner, 3D scan data of a first portion of a dentition of a patient including a first portion of a gingiva of the patient;

generate, using the intraoral scanner, blood oxygen saturation data for the first portion of the dentition of the patient including the first portion of the gingiva of the patient;

map the blood oxygen saturation data of the first portion of the gingiva of the patient to the 3D scan data; and display, on the display, the 3D scan data modified with an indication associated with the blood oxygen saturation of the first portion of the gingiva mapped to the 3D scan data.

17. The system of claim 16, the memory comprising instructions that when executed by the processor further cause the system to:

receive a blood oxygen threshold via user input.

18. The system of claim 16, wherein the indication further comprises feedback that highlights locations of blood oxygen saturation below a threshold.

19. The system of claim 16, wherein the indication further comprises feedback that colors locations based on the blood oxygen saturation data.

20. The system of claim 16, wherein the indication further comprises feedback indicating locations of blood oxygen saturation below a threshold and without feedback to second locations that are not the locations of blood oxygen saturation below the threshold.

* * * * *